(12) United States Patent
Gao et al.

(10) Patent No.: US 10,828,262 B2
(45) Date of Patent: Nov. 10, 2020

(54) BIOMEMBRANE, CLOSED STRUCTURE WITH BIOMEMBRANE CHARACTERISTICS OR CELLULAR COMPARTMENT DERIVED FROM NATURAL SOURCES AND/OR SELF-ASSEMBLY TECHNIQUES, PREPARATION METHOD AND APPLICATIONS THEREOF

(71) Applicant: Hangzhou UMotor Biotech Co., LTD., Hangzhou (CN)

(72) Inventors: Ying Gao, Hangzhou (CN); Yanming Wang, Hangzhou (CN); Jianliang Wei, Hangzhou (CN); Minzi Wang, Hangzhou (CN); Ye Cheng, Hangzhou (CN); Mingzhou Zhang, Hangzhou (CN); Liying Ye, Hangzhou (CN)

(73) Assignee: Hangzhou UMotor Biotech Co., LTD., Hangzhou (CN)

( * ) Notice: Subject to any disclaimer, the term of this patent is extended or adjusted under 35 U.S.C. 154(b) by 245 days.

(21) Appl. No.: 15/653,998

(22) Filed: Jul. 19, 2017

(65) Prior Publication Data
US 2019/0022018 A1   Jan. 24, 2019

(51) Int. Cl.
| | |
|---|---|
| *A61K 9/50* | (2006.01) |
| *A61K 8/9722* | (2017.01) |
| *A61K 8/9789* | (2017.01) |
| *A61K 8/99* | (2017.01) |
| *A61K 8/34* | (2006.01) |
| *A61K 8/35* | (2006.01) |
| *A61Q 19/00* | (2006.01) |
| *A61Q 19/02* | (2006.01) |
| *A61Q 19/08* | (2006.01) |
| *A61K 39/39* | (2006.01) |
| *A61L 27/36* | (2006.01) |
| *A61K 31/12* | (2006.01) |
| *A61K 31/343* | (2006.01) |
| *A61K 31/203* | (2006.01) |
| *A61K 38/22* | (2006.01) |
| *A61K 31/7048* | (2006.01) |
| *A61K 39/12* | (2006.01) |
| *A61K 39/00* | (2006.01) |
| *A61K 31/7088* | (2006.01) |

(Continued)

(52) U.S. Cl.
CPC .............. *A61K 9/5068* (2013.01); *A61K 8/11* (2013.01); *A61K 8/347* (2013.01); *A61K 8/35* (2013.01); *A61K 8/9722* (2017.08); *A61K 8/9789* (2017.08); *A61K 8/99* (2013.01); *A61K 9/5052* (2013.01); *A61K 31/12* (2013.01); *A61K 31/203* (2013.01); *A61K 31/343* (2013.01); *A61K 31/7048* (2013.01); *A61K 31/7088* (2013.01); *A61K 38/225* (2013.01); *A61K 39/0011* (2013.01); *A61K 39/12* (2013.01); *A61K 39/385* (2013.01); *A61K 39/39* (2013.01); *A61L 27/3604* (2013.01); *A61L 27/3612* (2013.01); *A61L 27/3637* (2013.01); *A61L 27/3654* (2013.01); *A61L 27/3687* (2013.01); *A61L 27/3691* (2013.01); *A61Q 19/00* (2013.01); *A61Q 19/02* (2013.01); *A61Q 19/08* (2013.01); *C12N 1/06* (2013.01); *C12N 1/12* (2013.01); *C12N 1/20* (2013.01); *C12N 5/0018* (2013.01); *C12N 5/04* (2013.01); *C12N 5/067* (2013.01); *C12N 5/0634* (2013.01); *C12N 15/88* (2013.01); *A61K 9/7007* (2013.01); *A61K 2039/53* (2013.01); *A61K 2039/54* (2013.01); *A61K 2039/541* (2013.01); *A61K 2039/55588* (2013.01); *A61K 2039/55594* (2013.01); *A61K 2039/57* (2013.01); *A61K 2039/575* (2013.01); *A61K 2800/56* (2013.01); *A61K 2800/62* (2013.01); *A61L 2430/06* (2013.01); *C12N 2500/70* (2013.01); *C12N 2503/02* (2013.01); *C12N 2525/00* (2013.01); *C12N 2760/18434* (2013.01)

(58) Field of Classification Search
None
See application file for complete search history.

(56) References Cited

U.S. PATENT DOCUMENTS 5,641,650 A * 6/1997 Turner ................. C07K 14/215
435/69.1
6,689,757 B1 * 2/2004 Craig ................. A61K 39/0011
424/93.2

FOREIGN PATENT DOCUMENTS

CN        104888230 A  *  9/2015

OTHER PUBLICATIONS

Cava et al., Extremophiles, 13:213-231 (2009) (Year: 2009).*
(Continued)

*Primary Examiner* — Thomas J. Visone
(74) *Attorney, Agent, or Firm* — Thomas|Horstemeyer LLP

(57) ABSTRACT

The present invention provides a method of preparing biomembrane, closed structure with biomembrane characteristics or cellular compartment, comprising the following steps: 1), acquire biological cells from natural tissues or natural biological species; 2), culture the cells obtained in step 1) massively in an appropriate environment; 3), acquire the lysates of cells in step 2), and extracting the biomembrane, closed structure with biomembrane characteristics and cellular compartment through differential centrifugation, density gradient centrifugation or dual-phase extraction individually or a combination of two methods or a combination of three methods thereof. The membrane is a natural biomembrane, closed structure with biomembrane characteristics and cellular compartment, which can be used for package of active ingredients in various fields.

4 Claims, 4 Drawing Sheets

(51) Int. Cl.

| | | |
|---|---|---|
| *A61K 8/11* | (2006.01) | |
| *C12N 5/04* | (2006.01) | |
| *C12N 5/078* | (2010.01) | |
| *C12N 1/20* | (2006.01) | |
| *C12N 1/06* | (2006.01) | |
| *C12N 5/071* | (2010.01) | |
| *C12N 1/12* | (2006.01) | |
| *C12N 15/88* | (2006.01) | |
| *C12N 5/00* | (2006.01) | |
| *A61K 39/385* | (2006.01) | |
| *A61K 9/70* | (2006.01) | |

(56) References Cited

OTHER PUBLICATIONS

Oshima et al., J. Biochem., 93:225-234 (1983) (Year: 1983).*
Lohia et al., J. Gen. Microbiol., 130:2027-2033 (1984) (Year: 1984).*
Cagdas et al., Application of Nanotechnology in Drug Delivery, Chapter 1 (2014) (Year: 2014).*
Gujrati et al., ACS Nano, 8(2):1525-1537 (2014) (Year: 2014).*
Burkhardt et al., 286(12):9977-9984 (2011) (Year: 2011).*
Caceres et al., PLOS ONE, 8(3):e58285 (2013) (Year: 2013).*
Degryse et al., Arch. Microbiol., 117:189-196 (1978) (Year: 1978).*
Eriksson et al, JBC, 284(49):33904-33914 (2009) (Year: 2009).*
Hancock et al., J. Bacteriol., 136(1):381-390 (1978) (Year: 1978).*
Hobb et al., Microbiol., 155(Pt 3):979-98 (2009) (Year: 2009).*
Jonca et al., J. Mater. Sci., 27(55):1-14 (2016) (Year: 2016).*
Yoshida et al., JBC, 259(1):112-123 (1984) (Year: 1984).*
Maier et al., J. Bacteriol., 183(2):800-803 (2001) (Year: 2001).*
Marani et al., Protein Sci., 15:884-889 (2006) (Year: 2006).*
Monteiro et al., J. R. Soc. Interface 11:0459 (2014) (Year: 2014).*
Munford et al., J. Clin. Invest., 70:877-888 (1982) (Year: 1982).*
Perry, Prokaryotes, 7:849-853 (Ch. 10.3), see Allen's Salt Solution (2006) (Year: 2006).*
Rumszauer et al., FEBS J., 273:3261-3272 (2006) (Year: 2006).*
Sercombe et al., Front. Pharmacol., 6:286 (2015) (Year: 2015).*
Tan et al., Theranostics, 5(8):863-881 (2015) (Year: 2015).*
Yang et al., Bio-protocol, 3(24):e2014 (2013) (Year: 2013).*

* cited by examiner

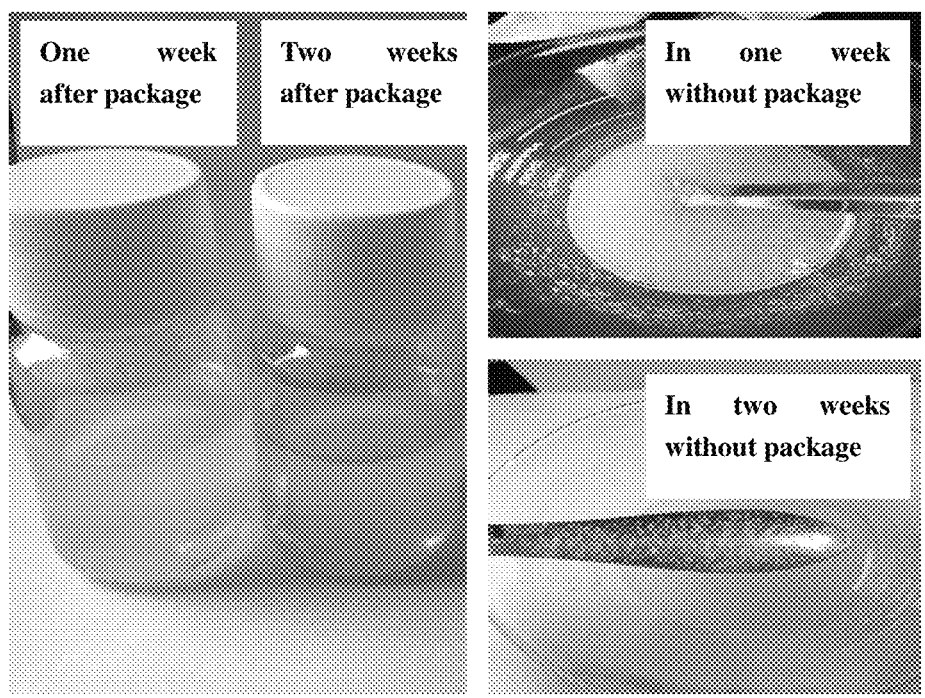
FIG. 1
FIG. 2A
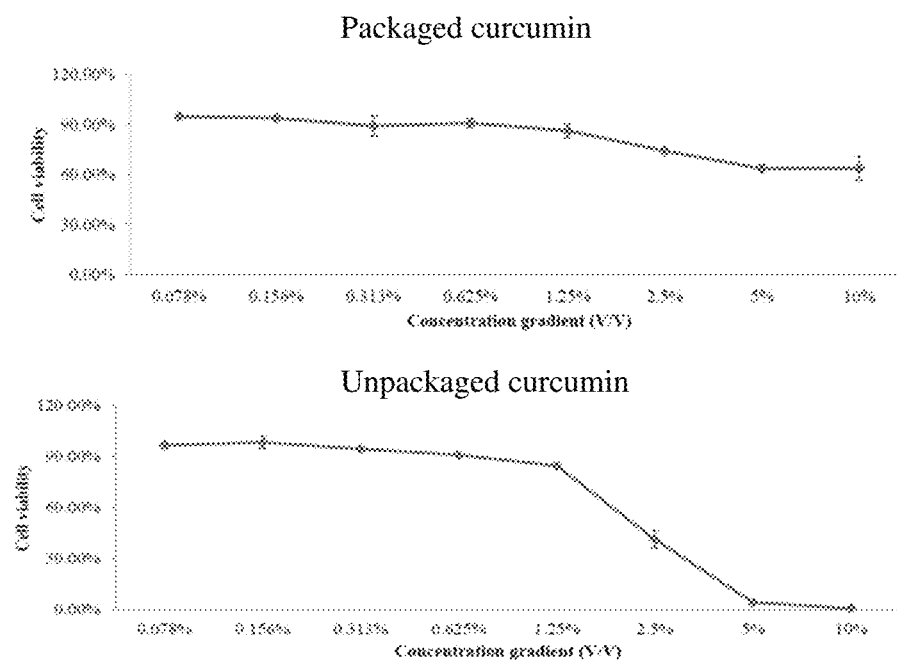
FIG. 2B

Packaged curcumin

Unpackaged curcumin

BIOMEMBRANE, CLOSED STRUCTURE WITH BIOMEMBRANE CHARACTERISTICS OR CELLULAR COMPARTMENT DERIVED FROM NATURAL SOURCES AND/OR SELF-ASSEMBLY TECHNIQUES, PREPARATION METHOD AND APPLICATIONS THEREOF

FIELD OF THE INVENTION

The present invention relates to the field of biomedicine and polymeric materials, in particular, to the biomembrane, closed structure with biomembrane characteristics and cellular compartment derived from natural sources and/or self-assembly technique, preparation method and applications thereof.

BACKGROUND

Biomembranes or biological membranes are the general term for all membrane structures that inhabit cells, organelle, and their environments, which are the important parts for intracellular communications and play a role of dividing and separating cells and organelles. Except some viruses, organisms have biomembranes. In addition to plasma membranes (also known as the cell membranes), eukaryotic cells have membrane systems that separate various organelles, including nuclear membranes, mitochondrial membranes, endoplasmic reticulums, lysosomal membranes, Golgi membranes, chloroplast membranes, vacuoles and peroxisome membranes, etc.

The biomembrane is a lamellar structure of lipid bilayer morphologically, and its main composition is lipid, and a small amount of proteins and carbohydrates. With the lipid bilayer structure, the biomembrane has the following functions: to regulate and control the materials in and out of cells, package and transport substances between different organelles in the cells, provide specific transport routes for certain reagents and signaling substances, and provide space for material storage trough the formation of cellular compartments.

The biomembrane has a variety of compositions, and it is difficult to separate and purify them. During early years, various artificial membrane structures composed of a single or several lipids are adopted such as monolayer membrane, cumulative membrane, liposome, plate bimolecular layer of lipid membrane, etc. In addition, the proteins can be embedded to form a reconstituted membrane, which is called "artificial membrane". The artificial membrane has been applied in practice, for example, efficiently separate and concentrate substances from seawater and other solution phases, uses as dialysis membrane for patients with kidney diseases, and for clinical diagnosis and treatment, etc. In recent years, an extended use of artificial membrane is to prepare liposome carrier drugs according to the characteristics of liposome of fusion with cell membranes, etc.

However, these artificial membranes, including liposomes, are susceptible to oxidation, leakage in vitro, with poor storage, and they are susceptible to degradation by some enzymes and phagocytosis by macrophages, and cannot reach the target tissues to give effective actions, all of which restrict their applications as carriers. In addition, with the addition of synthetic materials, the artificial membrane as a polymer material implanted in the human body will inevitably lead to rejection of body, which will limit its applications.

When living matters emerge on the earth and in the long-time evolution from simpliness to complexity, the emergence of biomembrane appears to be a leap, and after millions of years of evolution, the biomembrane has so fine structure and exquisite functional activity mechanism. The biomembrane itself has two largest properties, namely, membrane fluidity and asymmetry. The membrane fluidity means that the biomembrane is always in a movement state, which makes the lipid molecules in the membrane to exchange position constantly to guarantee that the membrane has the important functions of endocytosis, exocytosis, material transfer, cell fusion, etc. However, with the fluidity, the membrane will constantly deform, so the natural biomembrane is more unstable than the simple artificial membrane structure, and the artificial membrane including liposomes has poor stability and storage as carriers, and the package substances are easy to leak. In addition, biomembranes can be divided into two layers: cytoplasmic and non-cytoplasmic layers. The compositions and structures of the two layers of biomembrane are greatly different, and such difference is called biomembrane asymmetry. The biomembrane asymmetry produces important effect on the sorting of membranes, cell fusion, and intermolecular recognition, and such asymmetry is completely absent for artificial membranes.

In addition, the life is the highest form of material existence, and the most basic feature of life is to achieve self-regulation, self-reproduction and self-assembly through metabolism. Self-assembly is a constituent element of the system, which refers to the phenomenon of self-gathering to form a regular structure without human intervention. Self-assembly is the basis of the formation of various complex biological structures, and it is inseparable from the phenomenon of life. The biomembrane is a natural model for the study of self-assembly provided by organisms.

SUMMARY

In order to overcome the shortcomings of artificial membranes with application defects, one object of the present invention is to provide biomembranes, closed structures with biomembrane characteristics or cellular compartments derived from natural sources and/or self-assembly techniques; the second object is to provide a method of preparing biomembranes, closed structures with biomembrane characteristics or cellular compartments derived from natural sources and/or self-assembly techniques; and the third object is to provide the applications of aforesaid biomembranes, closed structures with biomembrane characteristics or cellular compartments. The biomembrane, closed structure with biomembrane characteristics or cellular compartment acquired through the aforesaid method can be applied to biomedical carrier technology, especially to transgenic vectors, drug carriers; or applied to the researches of cosmetic additives and cosmetic efficacy constituent carriers and product development; or the researches of vaccines and immunomodulators and product development; or the researches of polymer materials and product development, etc.

On one aspect of the invention is to provide a biomembrane or biomembrane fragment, and the biomembrane or biomembrane fragment is from natural species and in lipid bilayer structure morphologically, with the main compositions of lipids and proteins, and a small amount of carbohydrates bonded to lipids and proteins through covalent bonds.

In some preferred embodiments, these biomembranes comprise closed structures with a biomembrane characteristics or cellular compartments, or the biomembranes have closed structures with a biomembrane characteristics or cellular compartments.

In some preferred embodiments, biological sources can be from natural plants, animals or microbes.

In some preferred embodiments, the particle size of a biomembrane, closed structure with biomembrane characteristics or cellular compartment is from 10 nm to dozens of µm.

Preferably, the biomembrane, closed structure with biomembrane characteristics or cellular compartment include spherical, vesicular, rod-shaped, spiral single-layer or multi-layer, multi-chamber morphological structures.

Preferably, the biomembrane includes one or more of plasma membrane, nuclear membrane, mitochondrial membrane, endoplasmic reticulum, lysosomal membrane, Golgi membrane, chloroplast membrane and vacuole and peroxisome membrane.

Preferably, the cellular compartment is an organelle; and more preferably, the cellular compartment is one or more of mitochondria, chloroplasts, peroxisomes, lysosomes, endoplasmic reticulum, nucleus, Golgi and vesicles and microtubules.

In order to achieve the aforesaid second object, the present invention provides a method for acquiring a biomembrane.

A method of preparing the biomembrane, closed structure with biomembrane characteristics or cellular compartment as described in any one of aforesaid technical solution, comprising the following steps:
1) obtain biological cells;
2) culture the cells obtained in step 1) massively in an appropriate environment;
3) acquire the lysates of cells in step 2), and extract the biomembrane, closed structure with biomembrane characteristics and cellular compartment through differential centrifugation, density gradient centrifugation and dual-phase extraction individually or a combination of two methods or a combination of three methods thereof.

Preferably, the differential centrifugation extraction method comprises the following steps:
1. Centrifuge the cell lysate at 15,000-30,000×g for 10-30 min at 1-6° C., discard the precipitate and collect supernate;
2. Ultra-centrifuge the supernate at 100,000-200,000×g, 1-6° C. for 30-90 min, to discard the supernatant and collect the precipitate, to get the extracted biomembrane, closed structure with biomembrane characteristics or cellular compartment, re-suspend the precipitate in PBS/physiological saline containing 15-30% glycerol and preserve.

Preferably, the density gradient centrifugation extraction method comprises the following steps:
3. resuspend the resulting cell lysate precipitate in step 2, and add the resuspension solution to different concentrations of sucrose solutions, to ultra-centrifuge at 150,000-300,000×g, 1-6° C. for 60-90 min and collect the supernate;
4. then ultra-centrifuge the collected liquid at 100,000-200,000×g, 1-6° C. for 30-90 min, discard the supernatant and collect the precipitate, to get the extracted biomembrane, closed structure with biomembrane characteristics or cellular compartment; and re-suspend the precipitate in PBS/physiological saline containing 15-30% glycerol and preserve.

More preferably, the sucrose solution in the step 3 has a mass percent concentration in the range of 10% to 70%; preferably, the different mass percent concentrations of sucrose solution in step 3 are 10%, 20%, 30%, 40%, 45%, 50%, 55%, 60%, 65%, 70%.

Preferably, the dual-phase extraction method comprises the following features:
1, Prepare the aqueous dual-phase mixture of dextran/polyethylene glycol, and mix well in a separating funnel and stand at 4° C. for layering overnight, carefully separate the upper and lower layers, to make fresh top phase and bottom phase;
2, re-suspend the cell lysate precipitation obtained in step 5 and add to the aqueous dual-phase mixture, gently mix them upside down for 30-40 times evenly;
3, centrifuge at 2,000-4.000× for 5-10 min at 4° C., take the top phase and bottom phase to the two-phase system, to separate three times and combine the top phases, after diluted by 5-fold, centrifuge at 60,000-100.000×g for 30-90 min at 4° C., collect the precipitate, to get the biomembrane, closed structure with biomembrane characteristics or cellular compartment to be extracted, and re-suspend the precipitate in PBS/physiological saline containing 15-30% glycerol and preserve.

More preferably, the dual-phase is a dual-phase mixture of dextran/polyethylene glycol.

More preferably, the dual-phase comprises an aqueous dual-phase or an organic dual-phase, an aqueous phase solution and an organic phase solution, and the solvent is selected from any one of water, acetonitrile, acetone, tetrahydrofuran, methanol, ethanol, propanol or a combination thereof.

A method of preparing a biomembrane, closed structure with biomembrane characteristics or cellular compartment having self-assembly, wherein the method comprises the preparation method described in various technical solutions, and cover the materials of the acquired biomembrane, closed structure with the biomembrane characteristics and cellular compartment obtained in step 3) on the container wall in a form of dry membrane, then slowly inject water or buffer solution, slightly or violently vibrate, to get the required biomembrane, closed structure with biomembrane characteristics and cellular compartment by self-assembly.

Preferably, the material prepared in the step 3) is dissolved in chloroform and other similar organic solvent, such as), added to the container, evaporated under reduced pressure to make the biomembrane spread on the container surface, after evaporated to constant weight, PBS buffer solution is added and slowly shaken 0.5~3 h, ultra-centrifuged at 100,000~200,000×g for 30~90 min at 1~6° C., to discard the supernatant and collect the precipitates, to get the required biomembrane, closed structure with biomembrane characteristics and cellular compartment.

In order to achieve the third object, the present invention adopts the following technical solutions:

The applications of biomembranes, closed structures with a biomembrane characteristics or cellular compartments as described in any one of the aforesaid technical solutions are their intracellular membrane package, intracellular membrane package, surface adsorption, surface cross-linking, inter-membrane embedding and intracellular membrane package plus targeting on active ingredients.

Preferably, the active ingredient comprises a vaccine or active ingredient of immunoregulatory agents, a cosmetic or an active ingredient, a pharmaceutically active ingredient, a genetic material and cells or tissues.

The biomembrane, closed structure with biomembrane characteristics or cellular compartment in the present invention can be applied to biomedical carrier technology, especially to transgenic vectors, drug carriers and the researches of cosmetic additives and cosmetic efficacy constituent carriers and product development; or the researches of vaccines and immunomodulators and product development; or the researches of immunologic diagnosis and polymer materials and product development, etc.

The invention firstly proposes the ideas of the applications of closed biomembranes derived from natural sources and/or self-assembly techniques as carriers and/or immunomodulators in the chemical, pharmaceutical and cosmetic industries, and develop a variety of corresponding polymeric materials, pharmaceutical and cosmetic raw materials and intermediates.

BRIEF DESCRIPTION OF THE DRAWINGS

FIG. 1 shows the comparison chart of solubility of curcumin packaged by biomembrane.

FIGS. 2A and B shows the comparison chart of cytotoxicity of curcumin packaged by biomembrane.

DETAILED DESCRIPTION

Definitions and Interpretations

Figure 3:
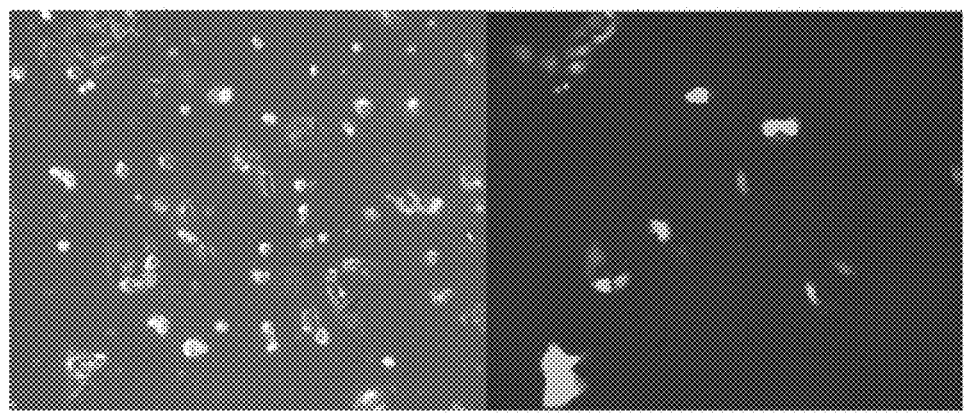
FIG. 3 shows the green fluorescence under the fluorescence microscope in 48 h after cell transfection, indicating successful transfection.

The terms in the present invention are understood according to ordinary definitions in the art, unless specially stated herein.

Biomolebrane: The "biomembrane" described in the present invention is distinguished from the "artificial membrane" in the conventional sense. The biomembrane herein is directly or indirectly derived from a natural organism or a specific tissue of an organism through the methods in the invention. The organisms described herein are existing individuals with living characteristics, including plants, animals, microorganisms, algae, and even viruses, etc. The tissue of an organism include an organ tissue of aforesaid animals, or a tissue of a part of a plant, or the animal or human blood, etc.

The "biomembrane" herein is a lipid bilayer structure morphologically and its compositions are lipids and proteins, and a small amount of carbohydrates bonded to lipids and proteins through covalent bonds. The "biomembrane" herein has closed structure with biomembrane characteristics or cellular compartment.

The particle size of a biomembrane, closed structure with biomembrane characteristics or cellular compartment is from 1 nm to dozens of μm, or 1-10 nm, or greater than 10 nm.

The biomembrane, closed structure with biomembrane characteristics or cellular compartment herein include spherical, vesicular, rod-shaped, spiral single-layer or multi-layer, multi-chamber morphological structures.

Similarly, the biomembrane includes one or more of plasma membrane, nuclear membrane, mitochondrial membrane, endoplasmic reticulum, lysosomal membrane, Golgi membrane, chloroplast membrane and vacuole and peroxisome membrane.

The "cellular compartment" herein is an organelle; and the cellular compartment is one or more of mitochondria, chloroplasts, peroxisomes, lysosomes, endoplasmic reticulum, nucleus, Golgi and vesicles and microtubules.

Closed structure with biomembrane characteristics: The "closed structure" herein means that some components that constitute the membrane can be automatically assembled into a membrane, or a closed membrane having the features of membrane under certain "condition"; when the "condition" does not exists, the components that constitute the membrane can be disassembled. These components or smallest units that constitute a membrane are also derived from natural living organisms or organisms, and acquired through the methods in the present invention.

Cellular compartment: Cells are the minimum independent units that make up a living organism, and a cell contains multiple organelles, and these organelles are in the cells that play different functions independently and separated by membranes, and these organelle membranes may include nuclear membranes, mitochondrial membrane, endoplasmic reticulum, lysosomal membrane, Golgi membrane, chloroplast membrane, vacuole, peroxisome membrane, etc. Here, the membrane that package the cellular compartment can be referred to as the "biomembrane" as described in the present invention.

Acquiring of Biomembrane or Cellular Compartment

Traditional techniques can be used to extract simple biomembranes, which usually obtain the mixture of various biomembranes or biomembrane fragments; in addition, they include some cell lysates, such as nucleic acid molecules, lipid molecules, oily molecules, and other "impurities", and these impurities often affect in vitro package properties of membranes. The mixtures containing these membranes can achieve some functions, such as re-package, but it is difficult to apply them to the products actually, and it is still in the laboratory stage. It is still a huge challenge to achieve similar functions of biomembranes through these in vitro extraction methods. In particular, it will take a long time to apply the biomembranes or the cellular compartments containing the membranes obtained by the in vitro extraction method to the particular products. In the present invention, based on this technical problem, the biomembrane or a cellular compartment containing a membrane is extracted through some tissues derived from a natural organism, to obtain a precise, pure structure or composition, or a biomembrane fragment, or a component that forms the membrane, and through the secondary processing in vitro, the membrane is formed again. These membranes through direct extraction and/or secondary processing have the functions similar to some biological membranes, retain some characteristics of membranes, thus, they are actually applied to many specific areas.

Method of Preparing Biomembranes

One aspect of the present invention is to obtain the target membrane compositions or biomembrane fragments or a complete membrane, but remove some unfavorable components or compositions that affect their in vitro applications. The biomembranes obtained by the present invention have lipid bilayer structures morphologically, and their constituent components are predominantly lipids and proteins, and a small amount of saccharides that are covalently bonded to the lipids and proteins, while other compositions are removed effectively, so that the resulting biomembranes have more effective roles and applications.

In some specific methods, a method of preparing biomembrane, closed structure with biomembrane characteristics or cellular compartment, comprising the following steps: 1), acquire biological cells from natural tissues or natural biological species; 2), culture the cells obtained in step 1) massively in an appropriate environment; 3), acquire the lysates of cells in step 2), then carry out separation and purification to obtain various biomembranes or mixture in the invention.

The methods for acquiring biomembranes in vitro herein include differential centrifugation, density gradient centrifugation and dual-phase extraction, individually or a combination of two methods or a combination of three methods thereof, to extract the desired biomembranes, closed structures with biomembrane characteristics and cellular compartments.

In some preferred embodiments, the differential centrifugation extraction method comprises the following steps:

centrifuge the cell lysate at the first high-speed to obtain a supernate and then centrifuge the supernate at a second speed less than the first high-speed to get the precipitate as the desired biomembranes.

Preferably, the first high-speed may be 1.5, 1, 2 or 3 times of the second speed.

Preferably, the first high-speed is usually 15,000-30,000× g, for example, 20,000×g, 25,000×g, 30,000×g, 35,000×g, or higher.

Further, in addition to the limited speed, centrifugation at low temperature is necessary.

In some preferred conditions, the centrifugation is carried out at 15,000-30,000×g, 1-6° C. for 10-30 min to discard precipitate and collect supernate; then the supernate is ultra-centrifuged at 100,000-200,000×g, 1-6° C. for 30-90 min, to discard the supernatant and collect the precipitate, to get the extracted biomembrane, closed structure with biomembrane characteristics or cellular compartment. The final precipitate is resuspended and preserved in PBS/physiological saline containing 15-30% glycerol.

In some preferred embodiments, preferably, the density gradient centrifugation method comprises the following steps:

resuspend the resulting cell lysate precipitate, and add the resuspension solution to different concentrations of sucrose solution, to ultra-centrifuge at 150,000-300,000×g, 1-6° C. for 60-90 min and collect the supernate;

then ultra-centrifuge the collected liquid at 100,000-200,000×g, 1-6° C. for 30-90 min, discard the supernatant and collect the precipitate, to get the extracted biomembrane, closed structure with biomembrane characteristics or cellular compartment. The precipitate is resuspended and preserved in PBS/physiological saline containing 15-30% glycerol.

or resuspend the resulting cell lysate precipitate, and add a first concentration of sucrose solution, a second concentration of sucrose solution and a third concentration of sucrose solution successively, and the first concentration is less than the second concentration and the third concentration is less than the first concentration.

More preferably, the sucrose solution has a mass percent concentration in the range of 10% to 70%; preferably, the different mass percent concentrations of sucrose solution in step 3 are 10%, 20%, 30%, 40%, 45%, 50%, 55%, 60%, 65%, 70%; or the molar concentration of a first concentration of sucrose solution is 0.1-0.5 mol/L, the molar concentration of a second concentration of sucrose solution is 1-3 mol/L; and the molar concentration of a third concentration of sucrose solution is 0.01-0.3 mol/L.

In some preferred embodiments, preferably, the density gradient centrifugation extraction process comprises the steps:

re-suspend the obtained cell lysate precipitation, after multiple times of centrifugation at first low-speed, collect the precipitate 1 to prepare suspension 1, then centrifuge the suspension 1 at a second high-speed for many times to get precipitate 2, and then suspend the precipitate 2 using a nonionic surfactant solution to get the suspension 2, at the same time, dilute suspension 2 with sucrose solution, transfer the diluted suspension 2 to the bottom of a centrifuge tube, and add high concentration and low concentration of sucrose solutions successively, centrifuge at a high speed (eg 28000×g-45,000×g) for 10-24 h at 4° C., and collect the desired biomembrane at the interface of high and low concentrations. The high concentration of sucrose is 20-35%, and the low concentration of sucrose is 2-10% (in mass percent).

In some preferred embodiments, preferably, the dual-phase extraction method comprises the following features:

Prepare the aqueous dual-phase mixture of dextran/polyethylene glycol, and mix well in a separating funnel and stand at 4° C. for layering overnight, carefully separate the upper and lower layers, to make fresh top phase and bottom phase; re-suspend the cell lysate precipitation obtained in step 5 and add to the aqueous dual-phase mixture, gently mix them upside down for 30-40 times evenly;

centrifuge at 2,000-4.000× for 5-10 min at 4° C., take the top phase and bottom phase to the two-phase system, to separate three times and combine the top phases, after diluted by 5-fold, centrifuge at 60,000-100.000×g for 30-90 min at 4° C., collect the precipitate, to get the biomembrane, closed structure with biomembrane characteristics or cellular compartment to be extracted, and re-suspend the precipitate in PBS/physiological saline containing 15-30% glycerol and preserve.

More preferably, the dual-phase is a dual-phase mixture of dextran/polyethylene glycol.

More preferably, the dual-phase comprises an aqueous dual-phase or an organic dual-phase, an aqueous phase solution and an organic phase solution, and the solvent is selected from any one of water, acetonitrile, acetone, tetrahydrofuran, methanol, ethanol, propanol or a combination thereof.

The cell lysate can be obtained through cell disruption, grinding, or chemical substance breaking, etc.

In some preferred embodiments, based on the biomembranes obtained through the aforesaid method, the methods for separation and purification of cellular compartments can be density gradient centrifugation, dual-phase extraction.

In some preferred embodiments, prepare the two-phase system, then prepare the resulting biomembrane precipitate as suspension, and then separate the cellular compartments. Of course, direct analysis of cellular compartments can be conducted for natural tissues and organisms.

Secondary Processing Method of Biomembranes

The membranes proposed herein (cell membranes, including the membranes of cellular compartments or cellular compartments) can be directly used in the package of active materials, however, in order to enhance the membrane property and stability after package, the present invention implements secondary processing of the membrane materials, fragments, components or minimum units and other composition or a mixture of a plurality of compositions extracted in vitro. The processing includes dissolution of mixed compositions, generally dissolved in organic solvent, e.g. chloroform, ether. After dissolved, these compositions such as complete membranes or biomembrane fragments, or membrane components, are mixed together, then spread on a solid surface, to remove the organic solvent, thereby forming a membrane with self-assembly closed properties.

Biomembranes can be self-closed under a certain solvent, and this self-closing characteristic can achieve a variety of purposes. For example, the active ingredient and membrane of secondary processing can be mixed, and under certain conditions, the active ingredient is automatically included in the membrane, or the membranes with self-closing properties can be formed, then package of active ingredients, embedding and adsorption on membrane surface can be performed.

In some preferred embodiments, the membrane composition mixture is dissolved in an organic solvent, added to the container, evaporated under reduced pressure to make the biomembrane spread on the container surface, and evaporated to constant weight, so that the organic solvent is completely volatile, which is very conducive to the production of the factory.

In some preferred embodiments, when evaporated to constant weight, add buffer solution to dissolve, the buffer solution can maintain the closure feature or membrane property of secondary processing membrane. This buffer can be PBS buffer solution. After dissolved, centrifuge under certain conditions to collect the precipitate, to get the biomembrane, closed structure with biomembrane characteristics and cellular compartment after secondary processing in the present invention.

In another aspect of the invention, a method of preparing a biomembrane, closed structure with biomembrane characteristics or cellular compartment having self-assembly, wherein the method comprises the preparation method described in various technical solutions, and cover the materials of the acquired biomembrane, closed structure with the biomembrane characteristics and cellular compartment on the container wall in a form of dry membrane, then slowly inject water or buffer solution, slightly or violently vibrate, to get the required biomembrane, closed structure with biomembrane characteristics and cellular compartment by self-assembly.

Preferably, the material prepared in the step 3) is dissolved in chloroform and other similar organic solvent, such as ether, etc.), added to the container, evaporated under reduced pressure to make the biomembrane spread on the container surface, after evaporated to constant weight, PBS buffer solution is added and slowly shaken 0.5~3 h, ultracentrifuged at 100,000~200,000×g for 30~90 min at 1~6° C., to discard the supernatant and collect the precipitates, to get the required biomembrane, closed structure with biomembrane characteristics and cellular compartment.

The container herein may be any container, such as the surface of a glass, ceramic, stainless steel container, etc.

Applications:

The biomembrane, closed structure with biomembrane characteristics or cellular compartment in the present invention (hereinafter referred to as "biomembrane") as a kind of basic material can be applied in many aspects, e.g. the biomembrane, closed structure with biomembrane characteristics or cellular compartment herein can be used for package of active substances (any substance), generally speaking, when the active substance exists alone, many adverse factors can affect the absorption and storage of the organisms, once the active substances are packed in biomembrane, effect of these adverse factors can be improved, e.g. these "active substances" can be applied to biomedical carrier technology, especially to transgenic vectors, drug carriers and the researches of cosmetic efficacy constituent carriers and product development; or the researches of vaccines and immunomodulators and product development; or the researches of immunologic diagnosis and polymer materials and product development, etc. The invention firstly proposes the ideas of the applications of closed biomembranes derived from natural sources and/or self-assembly techniques as carriers and/or immunomodulators in the chemical, pharmaceutical and cosmetic industries, and develops a variety of corresponding polymeric materials, pharmaceutical and cosmetic raw materials and intermediates.

Application of Drug Carriers:

1. Stability increase: packing of biomembrane lipid bilayer intracellular membrane and membrane can reduce the contact opportunities of drugs and external instable factors to enhance the stability. e.g. the acid-labile penicillin G can be easily destroyed by the gastric acid when orally taking; after packed with biomembrane, its stability and oral absorption effects can be enhanced. 2. Solubility increase: most drugs are insoluble chemical molecules, so, menstruums with many toxic and side effects need to be added to enhance solubility. The biomembrane as the carrier can pack the drugs, the amphipathicity of its lipid bilayer can dissolve the insoluble drug compositions into water soluble agents or lipid soluble agents. The paclitaxel (PTX) as a first-line broad-spectrum antitumor drug can be dissolved less in the water, so, a large amount of ethoxylate castor oil is added to the listed paclitaxel to increase solubility, while the ethoxylate castor oil with larger allergenicity can result in bronchospasm, shortness of breath, fatigue, hypotension and other problems; the paclitaxel packed in biomembrane will be of higher solubility and no allergic reactions. 3. Efficacy enhancement: biomembrane with cellular affinity and histocompatibility can make drugs fully permeated into target cells and tissues. The anti-tuberculosis drugs rifampin packed in biomembrane can be carried into human cells to kill the tubercle bacillus, so, its efficacy can be apparently enhanced compared to the traditional rifampin preparations. 4. Toxicity or irritation decrease: some chemotherapy drugs with strong vascular toxicity can result in chemotherapeutic phlebitis and common vascular complications. When these drugs packed in biomembrane are given with intravenous injection, the vascular toxicity can be apparently reduced. On the other hand, some drugs especially the antibiotics and anti-tumor drugs have bigger renal toxicity, those packed in biomembrane can be effectively concentrated in liver, spleen, marrow and organs with rich monocyte-macrophages, while less concentrated in heart and kidney than the free drugs. After drugs that are toxic to heart, kidney or normal cells are packed, their toxicities can be apparently reduced. The amphotericin B is a typical drug in treating systemic fungal infection, but it is toxic, especially to the kidney, its long-term application can damage kidney and circulating system, greatly limiting its application, after packed in biomembrane, its distribution in the body can be changed and toxicity can be apparently reduced. 5. Sustained release: most drugs have short acting time due to rapid metabolism or excretion in the body. After packed in biomembrane, the drug excretion and metabolism can be reduced, its detention time in blood can be prolonged, the drug can be slowly released in the body, so as to prolong the acting time. The calcitonin as polypeptide hormone secreted by thyroid C cells can be applied clinically in treating osteoporosis and other diseases, but the polypeptide drugs shall be given repeatedly due to short half-life period. After packed in biomembrane, the half-life period of calcitonin in the body can be extended by one fold. 6. Targeting: divided into passive targeting and active targeting. The passive targeting means the drugs packed in biomembrane can be swallowed as the foreign bodies by macrophages after entering the body, mainly swallowed by macrophages of monocyte-macrophage system and ingested, to form the passive targeting of liver, spleen and reticuloendothelial system. As for the meglumine antimouate for treating liver leishmaniasis, its concentration in liver can be enhanced by 500 times after packed in biomembrane. The active targeting means after the upper chain of biomembrane packing drugs connects to the targeting factor like ligand, the biomembrane can be specifically bonded with target cell receptor, to change the in vivo natural distribution of particles and then reach the specific target position. The Adriamycin as a kind of broad-spectrum antitumor drug is strongly toxic to the heart, even resulting in heart failure, but after packed in biomembrane with tumor target factor RGD, its toxicity on heart can be apparently reduced, and the lung cancer treatment efficacy can be at least enhanced by one time.

Transgenic transfection reagent: transgenic technology means the DNA fragment is transferred into specific microorganism and recombined with its genome, then artificial selecting and breeding of several generations is made from recombinant, to obtain the individual with stabile performance and specific genetic nature. On one hand, this technology can make the recombinant organisms with desired new property, to breed the new variety; on the other hand, the transgenic transfection technology is an important tool for studying transgene and gene expression, furthermore, it is a key step of gene treatment.

The ideal gene transfection reagent shall be of the following features: high-efficiency transfection, safety, low cytotoxicity, simple method, time saving and economical performance. But, the commonly used transfection reagent is of low transfection efficiency or bigger cytotoxicity, so, it is urgent to look for a kind of transfection reagent with high transfection efficiency and less cytotoxicity.

With the lipid bilayer structure, the biomembrane is of good similarity and compatibility with cell membrane and can be absorbed by cell membrance, fused by membrane or endocytosed by cell or occasionally directly penetrated, so, it can enter the cell as the exogenous substance such as DNA. DNA can be transmitted into the cell, to form the inclusion body or enter lysosome, a small amount of DNAs can be released from inclusion body to enter the cytoplasm, then enter the nucleus to be transcribed and expressed. Meanwhile, biomembrane is natural and has almost no cytotoxicity.

Cosmetics: cuticle is the outermost layer of the skin, where the lipid is a dense packed bilayer membrane and arranged in interphase manner with cuticle cells and interactively bonded by covalent way, to jointly form the main part of cuticle, it is also the major material basis of skin barrier function. Relevant studies showed that if the lipid is removed from epidermis cuticle, the skin barrier function will be lost and water content in skin will be apparently reduced, to result in dry skin; along with stopping of removal of skin lipid, the water content in cuticle will be recovered and dry skin will be improved. Hence, lipid existed among keratinocytes can fill in the intercellular spaces and act as an adhesive, to stop the skin water from diffusing and keep skin moisture and softness, meanwhile, it can prevent the foreign bodies from permeating skin, so, it is of barrier and moisturizing function.

Biomembrane with lipid bilayer structures morphologically can be applied in cosmetics with following functions: 1. Moisturizing effect: the Cholesterol, ceramide, palmitic acid and lipid constituent in the biomembrane can repair the lipid barrier of the skin, meanwhile, they can apparently improve skin conductance to strongly bond with water molecules and form the reticular formation in cuticle, so as to maintain skin moisture and improve skin elasticity. 2. Whitening effect: ceramide and lipid constituent in biomembrane as the signal molecule can regulate the peroxide in the cell and reinforce the peroxidation of lipid, to realize whitening; on the other hand, a large amount of unsaturated fatty acid contained in biomembrane can reduce the accumulation of melanin in the skin to whiten the skin. 3. Anti-aging effect: the phospholipid in biomembrane can enter the deep skin and bond with phospholipid-origin substance of cytomembrane in the deep skin, to fluidize the cell membrane, e.g. the unsaturated phospholipid containing linoleic acid and α-linolenic acid can increase the membrane mobility and permeability, so as to increase the metabolism of cells and activate the cells. When the cell tissues damage, disease or aging occur, it can boost the repairing and growth of epidermal growth factor to delay the cell aging.

Biomembrane as the efficacy constituent additives of cosmetics can play its distinctive role; meanwhile, biomembrane as the carrier of functional constituent can enhance the functional constituent by following results: 1. Stability increase: packing of biomembrane lipid bilayer intracellular membrane and membrane can reduce the contact opportunities of functional constituent and external instabile factors and enhance the stability. E.g. the alcohol structure of Vitamin A contains more unsaturated double bonds and is less stable to light and thermal stability, and can be easily oxidized after contacting with air, after packed in biomembrane, its stability can be enhanced. 2. Solubility increase: most cosmetics efficacy constituents are insoluble and hardly permeated into skin barrier to play its function, due to amphipathicity of lipid bilayer, biomembrane as the carrier can make the packed insoluble efficacy constituents permeated into the water soluble agents or lipid soluble agents. 3. Long-term effect: biomembrane as the carrier is of sustained-release function. Tests verified that biomembrane and packed drugs can be retained in blood for a longer time than the free drugs. 3. Absorption boosting: the cosmetics efficacy constituents must permeate the cuticle to reach corresponding site to nourish and improve the skin. The cuticle of human skin has strong barrier function, so, the large-molecule efficacy constituents can't be easily permeated. For the efficacy constituents packed in biomembrane (with similar structure as cuticle and strong affinity), the efficacy constituents increase via percutaneous permeation through carrying of biomembrane.

Vaccines Carrier and Immunomodulators:

development of biology, molecular immunology, gene engineering and other subjects has made vaccines more and more important, application of safe and effective adjuvants and carriers for vaccine delivery has been recognized by more and more people. The complete Freund's adjuvant, incomplete Freund's adjuvant, bacterial endotoxin, polyanion and mineral adsorbent that were commonly used before have been gradually discarded due to local and systemic toxicity, occurrence of unacceptable granuloma, short validity and low effectiveness. Alhydrogel adjuvant is safe and effective, but it can only realize humoral immunity and can't induce cellular immunity, furthermore, the inter-batch difference of antigen binding is bigger. So, obtaining a kind of safe and effective vaccine carrier that can effectively induce cellular immunity and humoral immunity and the new adjuvant technology has become a new challenge for vaccine application.

With the lipid bilayer structure, the biomembrane is of good similarity and compatibility with cell membrane and can be absorbed by cell membrance, fused by membrance or endocytosed by cell or occasionally directly penetrated, so, it can enter the cell as the exogenous substance. The biomembrane, by package or absorption, can act as the carrier of protein, nucleic acid, synthetic peptide, cell factor, bacteria, virus and other substances, meanwhile, biomembrane is a kind of non-pathogenic carrier with high safety coefficient. On the other hand, biomembrane can be effectively ingested by antigen-presenting cells (APCs), so as to arouse strong immune reactions, so, it has natural immunoadjuvant effect.

Biomembrane as the vaccines carrier and immunomodulator is of the following advantages: 1. High safety: biomembrane as the vaccine antigen expression and presenting carrier is a kind of non-immunogenicity and non-pathogenic carrier with high safety coefficient, at the vaccinated site, there exists no granuloma, so, repeated vaccination won't result in any adverse effect. Meanwhile, antigen about biomembrane carrier can't be detected on animals vaccinated by biomembrane, so, the possibility of biomembrane carrier in resulting in body immunologic rejection can be reduced. 2. Multi-functions: biomembrane carrier can directionally assemble protein, nucleic acid, synthetic peptide, cell factor, bacteria, virus and other substances, it can be applied in construction of traditional vaccines and new gene vaccines. 3. Compound type: biomembrane can directionally assemble the different antigens, nucleic acid and other substances, it can be used in research of multivalent compound vaccines and multivalent vaccines. 4. Efficient humoral immunity: DC (DC cell) is the currently found specialized antigen presenting cell with strongest functions, with lipid bilayer structure, biomembrane can, by cell membrance fusion, boost the ingestion of APC for antigen, to effectively activate the humoral immunity of corresponding antigen to generate antibody, so, it plays an important role in prevention of many infectious diseases. 5. Strong cellular immunity: most traditional vaccines can activate humoral immunity, but HIV, HCV and tumors need new therapeutic vaccines that can induce specific cellular immunity, which demands more about carrier and adjuvant. Biomembrane carrier with natural advantages can effectively activate DC cells and other antigen presenting cells, and realize strong cellular immunity activation by presenting exogenous antigen to MHC-1 and activating CD8+ and CD4+T lymphocytes of antigen. 6. Sustained release: linking of biomembrane carrier with antigen can delay the antigen release, to result in more thorough immune response and increase of immune effects.

Application of Biomembrane Vaccine:

1. Preventive vaccine of infectious disease: the humoral immunity is of apparent effect in preventing bacteria, virus and parasite infection. Biomembrane carrier antigen to mobilize the body's immune response to control and prevent the occurrence and prevalence of infectious diseases. 2. Therapeutic vaccine of infectious disease: for the body infected with virus, if the antibody generated by humoral immunity can't clear away the pathogens in the cell, the preventive vaccine is of no significance. Up to now, the virus disease can't be effectively treated with any drug, but its attack is mainly the infection in the cell, so, biomembrane carrier vaccine can induce the immune response of strongly specific cells, to provide effective routes for resolving this kind of problem. 3. Preventive vaccine of tumors: infection of persistent high-risk HPV can result in almost all invasive cervical cancers; infection of $H.$ $pylori$ ($H.$ $pylori$) is an important pathogenic factor of gastric cancer, mucosa-associated lymphoid tissue (MALT) and other diseases, the World Health Organization (WHO) has listed it as first-class carcinogen. This carcinogen is of clear etiology relation to tumor occurrence, the vaccine can be prepared by linking biomembrane carrier with related antigen or gene to vaccinate the susceptible healthy population or high-risk population, to control the occurrence of tumor. The research and development of preventive vaccine of tumor is expected to restrain tumor from the source.

IV Therapeutic vaccine of tumors: currently, its research is concentrated on immunotherapy and gene therapy, to enhance the body's immune response in different layers and boost cells to restore the regulating functions of itself's proliferation cycle, so as to treat the tumors. The research is mainly the enhancing of tumor immunity and breaking of immune tolerance. The preparation of peptide vaccine, recombinant carrier vaccine and DC vaccine by biomembrane carrier can induce stronger specific T cell reactions, so as to suppress tumor and reduce tumor size. 5. Vaccine of autoimmunity disease: the immunity injury of autoimmunity disease can result in occurrence of lesion of corresponding tissues and organs. As for the vaccine of autoimmunity disease, memorized T cell that has immune response on self tissue antigen is removed, and immunoregulation is combined, e.g. some cell factors with immunoregulation is added to systematically regulate the immune system. Through the biomembrane carrier, DNA vaccine, combined vaccine and polypeptide vaccine are prepared ensure its good application prospects in autoimmune disease vaccine.

Polymeric materials: since ancient times, people had an idea: whether an organ with lesion can be replaced just as machine parts replacement. In 1954, the United States Boston Medical hateweier•halisen and Joseph E. Murray successfully completed the first human organ transplant— kidney transplant surgery, initiating the new era of human organ transplant. But, the barriers to organ transplant has been troubling the doctors around the world, the transplanted organ is inevitably excluded by the body. Currently, patients receiving organ transplant shall take immunosuppressive drugs all their lives to avoid body exclusion, but such drugs will affect the whole immune system and reduce ability of patients to resist disease. To resolve this problem, scientists begin to develop a new method: culture the patient's local tissue or cell and polymeric materials used for stent in his/her corresponding site into the most "suitable" organ. such stent made of polymeric materials shall be of good cell and tissue compatibility to provide site for growth; meanwhile, the stent shall be of degraded characteristics, the degraded stent shan't be harmful to the human body and has no any sequela to tissue and organ. but presently, there exist no ideal materials for manufacturing the artificial organ stent.

The biomembrane is used as the substrate to culture cells or tissues, which can be used as artificial organ or stent of tissue regeneration repair for organ transplant, this kind of artificial organ or stent is of high safety and won't be excluded by the body, and its performance is almost same as the original tissue, with high utilization. So, it can provide abundant technology support for research and application of polymeric materials.

Particular Application Methods

The biomembranes prepared by the present invention can be used for the package of various kinds of different active substances, and the package methods are reverse evaporation method, ultrasonic emulsification method, electrostatic adsorption method, crosslinking method, high pressure homogenization method, pH gradient method, etc.

The biomembrane herein may be a biomembrane or a cellular compartment obtained according to the aforesaid method or a biomembrane after secondary processing.

The reverse evaporation method comprises the following steps: mix a biomembrane with amines, dissolved in a volatile organic solvent, then remove the volatile organic material by rotary evaporation under reduced pressure, and then mix with the active substance and incubate.

The package of the active substance in a biomembrane using a ultrasonic emulsification method comprises the following steps: prepare an active substance solution, conduct ultrasonic disruption of the organism, slowly add the active substance solution during the ultrasonic disruption process, then centrifuge to obtain a precipitate, which is the final package material. Preferably, the biomembrane is a biomembrane of a cellular compartment. A self-assembly biomembrane or a secondary processed biomembrane can be used for the electrostatic adsorption method.

DETAILED DESCRIPTION OF THE EMBODIMENTS

This invention is further described in combination with specific embodiments and drawings.

It is to be understood that these examples are merely illustrative of how the invention is achieved and not intended to limit the scope of the invention. The experimental methods that are not specified for the specific conditions in the following examples are generally in accordance with conventional conditions or the conditions recommended by the manufacturer.

Example 1: Extraction and Purification of Biomembrane

The biomembrane is extracted and purified according to the density gradient centrifugation method. The specific procedures are as follows:

(1) sacrifice the Zealand white rabbit that have been fasted for 18-24 h to take the liver, remove the great vessels, cut the liver into small pieces of about 2 mm$^3$, and rinse with saline until the tissue blocks become white;

(2) Prepare the homogenate: 1 mmol/L $CaCl_2$, 50 mmol/L HEPES (pH 7.4), 1 mmol/L PMSF, 2 μg/mL aprotinin, 2 μg/mL Antipain;

(3) Add liver tissues and homogenate to a 8-fold volume of homogenate according to the mass/volume ratio, and homogenize the tissues in an ice bath condition with an electric homogenizer at 15,000 rpm until tissue liquefaction;

(4) Filter the homogenate through four-layer gauge, centrifuge the filtrate at 1,000×g and 4□ for 10 min, and collect the precipitate;

(5) Sufficiently suspend the precipitate using sucrose solution A (0.3 mol/L sucrose, 50 mmol/L Tris, 3 mmol/L $MgCl_2$), add 9-fold volume of sucrose solution B (2 mol/L sucrose, 50 mmol/L Tris, 3 mmol/L $MgCl_2$) to the suspension, fill the centrifuge tube with sucrose solution C (0.25 mol/L sucrose, 10 mmol/L HEPES, 1 mmol/L EDTA) in the upper layer, and centrifuge at 90,000×g and 4° C. for 150 min, to collect the upper layer of membrane;

(6) Wash the membrane layer with a washing solution (50 mmol/L HEPES, 1 mmol/L PMSF, 2 μg/mL aprotinin, 2 μg/mL Antipain), and centrifuge at 90,000×g and 4° C. for 60 min, collect the precipitate to get the required biomembrane.

Example 2: Extraction and Purification of Biomembrane

The biomembrane is extracted and purified according to the density gradient centrifugation method. The specific procedures are as follows:

(1) Centrifuge 30 mL of fresh blood at 100×g and 4° C. for 10 min, suck the plasma and floccules on the erythrocyte surface layer with a sucker;

(2) Add 5-fold of pH 8.0 PBS buffer (by volume), centrifuge at 2,000×g, 4° C. for 15 min, discard the supernate, repeat 3 times;

(3) Add 40-fold of pH 8.0 PBS buffer (by volume) to the precipitate, stand 2 h at 4° C. for hemolysis;

(4) then centrifuge at 22,000×g, 4° C. for 20 min, repeat 4 times (to get the conventional biomembrane);

(5) Re-suspend the precipitates with a pre-cooled Triton X-100 buffer (containing 0.25 mmol/Lsucrose, 150 mmol/LNaCl, 1 mmol/LEDTA, 20 mmol/L Tris-HCl 和 1% Triton X-100), then dilute with equal volume of 80% (W/V) sucrose solution (cholesterol and sphingomyelin have long fatty acid chains, with a strong force between molecules, making its structure dense between disorder liquid and liquid crystal, and able to resist the extraction of surfactants at a low temperature); (other non-ionic surfactants can be used in addition to Triton X-100).

(6) Transfer 4 mL of membrane suspension to the bottom of the centrifuge tube, then add 4 mL of 30% and 3 mL of 5% sucrose solution, centrifuge at 38,000×g for 18 h at 4° C., collect at the interface of 5% and 30% sucrose, to get the required biomembrane.

Example 3: Extraction and Purification of Biomembrane (Similar to Example 2)

The biomembrane is extracted and purified according to the two phase partition method. The specific procedures are as follows:

(1) Screen normal corn seeds with uniform plumpness, sterilize them by immersed in 1% NaClO for 10 min, rinse and germinate under the constant temperature (25° C.) and dark conditions for 72 h;

(2) Take the corn epicotyls and add 2-fold extraction buffer according to the mass/volume ratio (5 mmol/L EDTA, 25 mmol/L Tris, 0.25 mmol/L sucrose, 1 mmol/L $MgSO_4$, 0.2% (W/V) BSA, 0.5% (W/V) PVP-10, 10% (W/V) glycerol, 15 mmol/L β-mercaptoethanol, 1 mmol/L PMSF, 1 mmol/L DTT), grind in ice bath condition until liquefaction;

(3) filter the grinding fluid through four-layer gauze, and centrifuge the resulting filtrate at 12,000×g, 4° C. for 15 min, and take the supernate;

(4) Centrifuge the supernate at 80,000×g, 4° C. for 30 min, and collect the precipitate;

(5) fully suspend the precipitate using the suspension (25 mmol/L Tris, 0.25 mmol/L sucrose, 0.2% (W/V) BSA, 10% (W/V) mannitol, 1 mmol/L DTT);

(6) add suspension to the two-phase system (10 g of two-phase system containing: 1.7 g sucrose, 0.003 g DTT, 2.25 mL water, 50 mmol/L KCl 0.5 mL, 1.63 PEG, 3.25 g Dextran T-500, 200 mmol/L PBS 0.5 mL), shake up and down for 50 times, centrifuge at 4,000×g for 5 min at 4° C., take the top phase and bottom phase to the two-phase system, to separate three times and combine the top phases, after diluted by 5-fold, centrifuge at 80,000×g for 60 min at 4° C., collect the precipitate, to get the required biomembrane.

Example 4: Extraction and Purification of Biomembrane

The biomembrane is extracted and purified according to the differential centrifugation method. The specific procedures are as follows:

(1) *Chlamydomonas* subcaudata is isolated and purified from the Antarctic sea ice; (the temperature of the *Antarctica* in the winter can be dropped from ice-water interface −2° C. to ice-air interface −50° C.; when frozen, the ice algae need to bear the pressure higher than three times of the salinity of the sea water, while the salinity of the brine precipitated by the sea icing process is very high; in addition, the formation of sea ice and increased ice and snow covering will significantly reduce the light. Low temperature, less light and high salinity almost affect all major aspects of photosynthesis, therefore, in order to survive and reproduce in this cold environment, the ice algae should undergo complex, adaptive physiological, metabolic and genetic changes, and its membrane structures and membrane compositions are greatly changed.)

(2) Inoculate the *Chlamydomonas* subcaudata to a medium according to the ratio of 1:100 (10 L of medium contains 21.2 g NaCl, 3.6 g $NaSO_4$, 0.6 g KCl, 0.3 g $NaHCO_3$, 0.1 g KBr, 0.1 g $H_3BO_3$, 0.1 g NaF, 9.6 g $MgCl_2.6H_2O$, 1.0 g $CaCl_2$, 0.1 g $SrCl_2.6H_2O$), and culture in a light-controllable incubator at −4° C., 1300-1900lx, with a light cycle of 12-hour light/12-hour dark for 14 days, shaking 4-5 times every day;

(3) Centrifuge the ice algae medium at 4,000 rpm, 4° C. for 20 min, collect the ice algae precipitates, and quickly rinse it with the precooled distilled water twice, to remove the extracellular viscous matters, surface salts and impurities in the culture medium;

(4) Add the above collected ice algae precipitates to a 4-fold homogenate buffer according to the mass/volume ratio (0.5 mol/L KOH, 0.5 mol/L sucrose, 3 mmol/L EDTA, 0.6% PVP, 1 mmol/L PMSF, 1 mmol/L DTT, 5 mmol/L ascorbic acid, 0.6% BSA), and crack cells using an extruded-type cell cracker;

(5) Centrifuge the resulting cell homogenate at 8,000 rpm, 4° C. for 20 min, to collect the supernate;

(6) Centrifuge the supernate at 145,000×g, 4° C. for 60 min, to collect the precipitate, i.e. the required biomembrane.

Example 5: Extraction and Purification of Biomembrane

The biomembrane is extracted and purified according to the differential centrifugation and density gradient centrifugation method (described in Example 8). The specific procedures are as follows:

(1) *Thermus Thermophillus* is separated and purified from U.S. Yellowstone National Park Spa Pool; (Thermophilic bacteria, also known as high temperature bacteria, thermophilic microorganism, is a kind of microorganisms living in the high temperature environment, such as the crater and its surrounding areas, hot springs, etc. In order to keep normal metabolism and growth without inactivation under high temperature, the membrane structure and compositions of Thermophilic bacteria have undergone tremendous changes: for the chemical compositions of the Thermophilic bacteria biomembranes, the total content of lipids increases with the increased ambient temperature, and the fatty acids of high melting point also increase, to increase the membrane stability; in addition, the bilayer lipids in thermophilic bacteria are covalently cross-linked, greatly enhancing their heat resistance.)

(2) inoculate *Thermus Thermophillus* to a medium according to the ratio of 1:100 (10 L of medium contains 26 g $(NH4)_2SO_4$, 2.47 g $MgSO_4.7H_2O$, 2.8 g $KH_2PO_4$, 0.74 g $CaCl_2. 2H_2O$, 0.19 g $FeCl_3.6H_2O$, 0.018 g $MnCl_2.4H_2O$, 0.044 g $Na_2B_4O_7.10H_2O$, 0.002 g $ZnSO_4.7H_2O$), place to an incubator and culture 24 h at 150 rpm, 60° C.;

(3) centrifuge to collect thalli for 30 min at 4,000 rpm and 4° C.;

(4) re-suspend thalli with a homogenate buffer (20 mmol/L Tris-Cl pH8.0, 100 mmol/L NaCl, 2 mmol/L $MgCl_2$, 1 mmol/L DTT), centrifuge to discard the supernatant for 10 min at 6,000 rpm and 4° C.;

(5) add homogenate buffer to re-suspend the precipitate (add 10 ml of buffer in about 1 g), then add PMSF with a final concentration of 1 mmol/L, break under ice bath and ultrasound condition (amplitude of 55%, ultrasound 5 s, stop 8 s);

(6) centrifuge the broken thalli at 25,000×g for 30 min at 4° C., to discard the precipitate and collect the supernatant;

(7) ultra-centrifuge the supernatant at 145,000×g for 1 h at 4° C., collect the precipitate to get the required biomembrane.

Example 6: Separation and Purification of Cellular Compartment (Similar to Example 2)

The cellular compartment is separated and purified according to the density gradient centrifugation method. The specific procedures are as follows:

(1) select 10 g of spinach leaves with healthy growth, and preferably growing in several successive sunny days, wash clean to remove midrib, add 6 times of homogenate buffer (by volume) (50 mmol/L potassium phosphate buffer, 0.3 mmol/L sorbitol, 2 mmol/L EDTA, 1 mmol/L $MgCl_2$, 1 mmol/L $MnCl_2$, 1% BSA, 1 mmol/L DTT) according to the mass/volume ratio, and grind under ice bath;

(2) prepare the Percoll separating solution (50 mmol/L HEPES-KOH, 0.3 mmol/L sorbitol, 2 mmol/L EDTA, 1 mmol/L $MgCl_2$, 1 mmol/L $MnCl_2$, 1% BSA, 3% PEG 6000, 1% Ficoll), pre-centrifuge at 30,000×g for 20 min at 4° C.;

(3) filter the grinding fluid through a four-layer gauze, centrifuge at 30,000×g for 15 min at 4° C., collect the precipitate, and suspend the precipitate with 2 ml homogenate buffer, and place to the Percoll separating solution centrifuged in step (2), centrifuge at 15,000×g for 20 min at 4° C., such the lower layer, to get the required cellular compartment, which is rich in chloroplast.

Example 7: Separation and Purification of Cellular Compartment

The cellular compartment is separated and purified according to the dual-phase extraction method. The specific procedures are as follows:
(1) Preparation of aqueous dual-phase system: mix the mixture (containing 90 g 20% (W/W) Dextran T-500, 45 g 40% (W/W) PEG 3350, 33.9 g sucrose, 7.5 g 0.2 mmol/L PBS, 0.45 g 2 mmol/L KCl per 300 g) uniformly, to make equal concentration of aqueous dual-phase mixture of dextran/polyethylene glycol (Dextran T-500/PEG 3350), mix well in a separatory funnel, standing for layering at 4° C. overnight, carefully separate the upper and lower layers, to prepare fresh top phase and bottom phase, then store in 4° C. respectively for the subsequent purification;
(2) re-suspend the biomembrane precipitate obtained in Example 4 using resuspension buffer (5 mmol/L PBS, 0.33 mol/L sucrose, 3 mmol/L KCl, 1 mmol/L DTT, 1 mmol/L PMSF, 0.1 mmol/L EDTA);
(3) Add the above re-suspension to the aqueous dual-phase mixture of Dextran T-500/PEG 3350 prepared in step (1) according to a mass ratio of 1:3, gently reverse 30-40 times to mix well;
(4) centrifuge the mixed solution at 1,500 rpm for 10 min at 4° C., continue to take the top phase solution and bottom phase solution to the two-phase system, after separated 3 times, combine the top phase separation solution, dilute 5 times, centrifuge at 100,000×g for 60 min at 4° C. and collect the precipitate, to get the required cellular compartment, with rich thylakoids (the growth and reproduction of ice algae require photosynthesis and the thylakoid is the organ of photosynthesis. The thylakoid of the ice algae is not a simple "cup", but distributed in the whole cell outside the cell nucleus region in the form of lamellae, so that the photosynthesis of cells can be efficient no matter which direction; in addition, the thylakoid membrane of *Chlamydomonas* subcaudata has a significantly higher unsaturated fatty acid content than that of ordinary thylakoid membrane, this is because *Chlamydomonas* subcaudata needs to overcome the adverse effects of low light through desaturation of thylakoid membrane lipids).

Example 8: Separation and Purification of Cellular Compartment

The cellular compartment is separated and purified according to the density gradient
(1) Add 1.5 ml of 60% sucrose, 6 ml of 40% sucrose and 1.5 ml of 20% sucrose to a density gradient centrifugation tube from bottom to the top;
(2) Add 1 ml of biomembrane precipitate obtained in Example 5 to the density gradient centrifugation tube, centrifuge at 38,000 rpm, 4° C. for 1.5 h, and collect the intermediate layer of membrane;
(3) Wash the collected layer of membrane, centrifuge at 145,000×g, 4° C. for 90 min to get the precipitate, which is the required cellular compartment and rich in chromoplastids (the chromoplastid is a kind of plastid with pigments, and the chloroplast is a chromoplast, but usually the chromoplasts other than chloroplast are called chromoplastids. The chromoplastids do not have photosynthesis, and their main functions are to enrich starch and lipids, rich in lipid and plastoquinone. The plastoquinone is a kind of liposoluble quinone compounds in the nature, and its structure is similar to vitamin K, vitamin E and coenzyme Q10. It is involved in energy production and activation in human body cells and can activate human cells and cell energy.)

Example 9 Preparation of Biomembrane

The biomembrane is prepared by self-assembly techniques. The specific procedures are as follows:
(1) Dissolve the biomembrane obtained in the above Example 2 in sufficient ether at 1:10;
(2) Add the above biomembraneether solution a round-bottom flask and evaporate under reduced pressure to spread the biomembrane on the surface of the flask, after evaporated to a constant weight, add the PBS buffer solution equal to 2-fold biomembrane in volume, and slowly shake 2 h;
(3) Centrifuge the above solution at 6,000 rpm, 4° C. for 20 min, collect the precipitate, and re-suspend the precipitate using a resuspending buffer (20 mmol/L Tris, 0.1 mol/L NaCl, 2 mmol/L $MgCl_2$, 1 mmol/L DTT);
(4) Ultra-centrifuge the re-suspension at 150,000×g, and 4° C. for 60 min, discard the supernatant and collect the precipitate, that is, the biomembrane obtained by self-assembly techniques, with the closure property.

Of course, in addition to the biomembrane obtained by organisms in Example 1 through self-assembly techniques, the biomembrane can be obtained using similar or same method in other examples.

Example 10 Intracellular Membrane Package (Membrane Formation and Package)

The DNA package is carried out in biomembrane using reverse evaporation method. The specific procedures are as follows:
(1) Mix the biomembrane obtained in Example 2 and octadecylamine (or (2,3-dioleoyl-propyl)-trimethylamine) in a ratio of 10:1 (volume ratio), and dissolve in a 4-fold volume of chloroform (or ether, methanol, etc.), then evaporated under reduced pressure (37° C., 200 rpm) on a rotary evaporator to remove chloroform;
(2) mix 1 mL of GFP eukaryotic expression plasmid at 280 ug/mL with 1 mL of PBS at 100 mmol/L in equal volume;
(3) Slowly add the above plasmid containing PBS into the biomembrane in above step (1), incubate at 38° C. water bath for 20 min, to get the transgenic vector packaged with the GFP plasmid.

Example 11 Intracellular Membrane Package

The drug package is carried out in biomembrane using the ultrasonic emulsification method. The specific procedures are as follows:
(1) Mix the curcumin and PEG-400 at a ratio of 1:4 (weight ratio) at room temperature;
(2) Place the cellular chamber obtained in Example 5 in an ice bath environment and perform ultrasound using an ultrasonic processor, slowly add the curcumin solution obtained in step (1) dropwise until the final volume ratio is 1:1, and then implement ultrasonic emulsification;
(3) The amplitude of ultrasonic probe is 50%, with working time 30 s and an interval 30 s, 45 cycles;
(4) Centrifuge the above liquid at 100,000×g, 4° C. for 20 min, discard the supernatant, collect the precipitate, to get the packaged curcumin carrier.

Example 12 Surface Adsorption

The vaccine is prepared by biomembrane surface adsorption of viruses with an electrostatic adsorption method. The specific procedures are as follows:
(1) re-dissolve the biomembrane obtained in Example 9 through self-assembly techniques in PBS buffer at pH 5.8 in a volume ratio of 1:2, and shake well;
(2) Fully mix the inactivated Porcine circovirus (PCV2) and the above-mentioned biomembrane re-dissolved in the PBS at a ratio of 8:1, froze overnight at −30° C., then freeze-dried overnight at −60° C., to get the required vaccines.

Example 13 Surface Cross-Linking

Artificial organs are prepared on the biomembrane surface cross-linking cells with the crosslinking method. The specific procedures are as follows:
(1) Prepare the biomembrane template by crosslinking the biomembrane with solution of glutaraldehyde solution through self-assembly techniques in Example 9;
(2) Culture the human meniscus fibrochondrocytes in an incubator (5% $CO_2$, 37° C.), and take the second generation of cells to make the cell suspension with F-12 medium (containing 10% calf serum);
(3) Place the dried biomembrane template after sterilized by UV ray to a 6-well culture plate, add the above cell suspension to immerse, and place to a constant temperature incubator for shaking 2 h at 37° C.; take out the cell plate and culture in a $CO_2$ incubator (5% $CO_2$, 37° C.) for 2 days, to get the required artificial meniscus.

Example 14: Inter-Membrane Embedding (Organelle)

The drug is embedded between biomembrane bimolecular layers using the high-pressure homogenization method. The specific procedures are as follows:
(1) Melt the cellular compartments obtained in Example 7 and retinoic acid at 65° C., and make the colostrum by high shear with a high-shear dispersing emulsifier;
(2) Mix the colostrum with 65° C. distilled water dissolved with Tween −80, cycle 15 times at high pressure homogenizing condition with the pressure of 80 MPa, then naturally cool down to room temperature, to get the required the drug carrier packaged with retinoic acid.

Example 15: Intracellular Membrane Package Plus Targeting

The drug package is carried out in a biomembrane using a pH gradient method and the protein on the biomembrane is linked to the target factor. The specific procedures are as follows:
(1) dissolve the biomembrane obtained in Example 5 in an aqueous solution of 0.3 mol/L citric acid (pH=4), and then rotate under reduced pressure to form the biomembrane membrane on the container wall;
(2) Adjust the above biomembrane with 1 mol/L sodium carbonate solution to make the pH of suspension to 7.8, so that a proton gradient inside and outside the biomembrane can be formed, used as a carrier for active loading;
(3) Dissolve the adriamycin in 1 mol/L HEPES buffer solution (pH=7.8) at 60° C. to form a saturated solution of adriamycin;
(4) Mix the biomembrane suspension and adriamycin saturated solution, and incubate 20 min at 60° C. water bath, centrifuge the mixed solution at 80,000×g, and 4° C. for 60 min, discard the supernatant and collect the precipitate, to get the required drug carrier packaged with adriamycin;
(5) Label the targeting factor iRGD with avidin and modify the biombrane carrier carrying the adriamycin to biotin, through the biotin-avidin system, ligate the iRGD into the biombrane carrier containing adriamycin, to get the required drug carrier packaged with adriamycin, with the targeting property.

Example 16: Beneficial Effect of Drug Carrier (Improving Drug Solubility)

(1) Gently shake the carrier packaged with curcumin obtained in Embodiment 11 in 5% Triton X-100 at 37° C. overnight, and dilute with 100-fold of methanol (by volume);
(2) Conduct test on the content of curcumin by HPLC, to calculate the content of curcumin in the carrier, which is 7.2%;
(3) Simply mix the curcumin (content: 7.2%) and carrier as a control, and store the carriers packaged with curcumin and the control in sealed, colorless glass bottles a respectively, place one week and two weeks at 37° C. respectively, then conduct stability test;
(4) The results in FIG. 1 show that the solubility of curcumin packaged by biomembranes is significantly higher than that of the mixture.

Example 17: Beneficial Effect of Drug Carrier (Improving Drug Stability)

Same as the Example 16

Example 18: Beneficial Effect of Drug Carrier (Reducing Drug Toxicity)

(1) Simply mix the curcumin (content: 7.2%) and carrier as a control as mentioned in the above, and dilute the packaged curcumin and control into different-dilutability solutions respectively;
(2) Utilize curcumins of different dilutabilities and curcumin-biomembrane carrier to co-incubate with epidermis cell;
(3) The results in FIGS. 2A and B show that cytotoxicity of curcumin packaged by biomembranes is apparently lower than that of mixture.

Example 19: Beneficial Effect of Drug Carrier (Improving Curative Effect of Drug)

Reverse evaporating method is used to package drug in biomembrane, the specific procedures are as follows:
(1) Dissolve the biomembrane obtained in the abovementioned example 5 into chloroform of 4 times volume, then decompress, rotate and evaporate on rotary evaporators (37° C., 200 rpm) to remove chloroform;
(2) Dissolve rifampicin into PBS, and add ether to dissolve into biomembrane in the step (1), then blend it with rifampicin in equal volume, and place the compound into 50° C. water for incubation for 20 min to get the drug carrier for packaged rifampicin required;
(3) Slightly shake the drug carrier of packaged rifampicin obtained in the above mentioned step by using 5% Triton X-100 at 37° C. to stay overnight for demulsification, and dilute into methyl alcohol with volume ratio 100:1, determine the content of rifampicin by means of high performance liquid chromatography, the content of rifampicin in carrier is 10.2%;
(4) Take 20 health mice without limitation of female and male, with weight of 25-35 g for each, inject 0.1 mL $H_{37}Rv$ *Mycobacterium tuberculosis* suspension with concentration of $1.75\times10^8$ colony-forming unit (CFU)/mL from caudal vein, then divide the mice into group A and B randomly, 10 mice for each group, 14 days after injection;

(5) As for group A, implement intravenous injection for drug carrier of packaged rifampicin obtained in the abovementioned step once every three days, 10 ul for each time; as for group B, inject the same dosage of rifampicin drug as control;

(6) Kill the mice three weeks after injection, take spleen homogenate to cultivate on Lowenstein-Jensen culture medium slope with proper concentration, and compute the number of colony 6 weeks later, then compute CFU;

(7) The results show that the curative effect of rifampicin which is packaged with biomembrane improves one time than that of ordinary rifampicin.

Example 20: Beneficial Effect of Drug Carrier (Improving Curative Effect of Drug, Involved Different Dosage Forms)

(1) Take 20 health new zealand white rabbit without limitation of female and male, with weight of 1.5-2.0 kg for each, then divide the mice into group A and B randomly, 10 mice for each group.

(2) After inject 3% pentobarbital sodium into vein of ear edge for anesthesia, incise bulbar conjunctiva at superior temporal quadrant, and implement gas-compressed vitreous, namely inject 0.1 mL $C_3F_8$ gas with No. 30 needle into center of vitreous cavity 3 mm away from corneal limbus, so as to press vitreous body to the periphery when gas expands. 3 d later, implement anesthesia in the same way, and make a mattress preset suture with 5-0 silk sutures at previous needle-in place, use micro vitreum retina knife to puncture sclera to give out gas, then inject L929 cell suspension, finally establish PVR experiment model;

(3) After injection of cells, inject 0.2 ml drug carrier of packaged retinoic acid obtained in the example 14 for group A, and inject 0.2 mL retinoic acid silicone oil drug obtained in the market as control, then ligature preset sutures;

(4) After injecting L929 cell into vitreous cavity of lagophthalmos, vaporific turbid area is formed immediately in rear vitreous body, then offwhite strap is formed gradually about a week later to connect to papilla and medullary ray. In the $28^{th}$ day after operation, use tropicamide for mydriasis, and indirectly check vitreous body with ophthalmoscope. Then divide vitreous body into four grades from 0 to III according to turbid degree. Grade 0: the vitreous body is not turbid; grade I: the vitreous body is slightly turbid, which has no influence observation of eye ground; grade II: the vitreous body is moderately turbid, but eye ground can be seen through the turbid vitreous body; grade III: the vitreous body is severely turbid, but eye ground cannot be seen. Then implement statistics of occurrence rate of grade I, II, III. The experimental results show that the turbid degree of vitreous body for sample group compared to control group is light, with statistic difference.

| Grade | retinoic acid-biomembrane group | retinoic acid-silicone oil group |
|---|---|---|
| 0 | 0 | 0 |
| I | 8 | 5 |
| II | 9 | 7 |
| III | 3 | 8 |

Example 21: Beneficial Effect of Drug Carrier (Improving Long Residual Action)

Reverse evaporating method is used to package drug in biomembrane, the specific procedures are as follows:

(1) Dissolve the biomembrane obtained in the example 6 into chloroform with volume ratio by 4:1, implement decompression rotary evaporation on rotary evaporator (37° C., 200 rpm) to remove chloroform;

(2) Dissolve calcitonin in PBS, add ether to dissolve the biomembrane in step (1), and blend with the above mentioned in equal volume, then place the compound into 50° C. water to incubate for 20 min, then the required drug carrier of packaged calcitonin is obtained;

(3) Dissolve by ultrasound the drug carrier of packaged calcitonin obtained in the abovementioned step with methyl alcohol with volume ratio of 500:1, blow with 37° C. nitrogen and use PBS to re dissolve it, and determine the content of calcitonin with immunoluminometric assay, the content is 8.6%;

(4) Take 10 health new zealand white rabbit without limitation of female and male, with weight of 1.5-2.0 kg for each, then divide the mice into group A and B randomly, 5 mice for each group.

(5) Inject 10 ml drug carrier of packaged calcitonin obtained in the abovementioned step through vein for group A, and inject the same dosage of calcitonin for group B as control;

(6) The results show that the in vivo half-life period of calcitonin of packaged biomembrane is 4 hours, while the half-life period of ordinary calcitonin is 2 hours, therefore the long residual action improves by one time.

Example 22: Beneficial Effect of Drug Carrier (Drug Passive Targeting/Reducing Toxicity)

The ultrasound emulsion process is used to package drug in biomembrane, the specific procedures are as follows:

(1) Dissolve the amphotericin B into ethyl alcohol to from saturated solution;

(2) Blend the abovementioned saturated solution of amphotericin B with cellular compartment obtained in the example 6 to implement ultrasonic emulsification with ultrasonic disruption instrument under the ice environment for 20 times with working for 30 s and interval of 30 s, the amplitude of ultrasonic probe is 40%;

(3) Centrifuge emulsion under the conditions of 100,000× g, 4° C. for 20 min, remove the supernatant, collect the sediment to get the drug carrier of required packaged amphotericin B;

(4) Slightly shake the drug carrier of packaged amphotericin B obtained in the abovementioned step by using 5% Triton X-100 at 37° C. to stay overnight for demulsification, and dilute into methyl alcohol with volume ratio 100:1, determine the content of amphotericin B by means of high performance liquid chromatography, the content of rifampicin in carrier is 8.3%;

(5) Take 30 health mice without limitation of female and male, with weight of 18-22 g for each, then divide the mice into group A and B randomly, 15 mice for each group.

(6) Inject 0.2 mg drug carrier of packaged amphotericin B mentioned above into caudal vein of mice for group A, and inject the same dosage of amphotericin B for group B as control, then kill the 3 mice for each group after collecting blood from heart 0.5, 1.0, 1.5, 2.0 and 5.0 h after administration, and take out the liver, kidney, spleen and other organs to determine the content of amphotericin B;

(7) The results show that the drug distribution of amphotericin B of packaged biomembrane in kidney is apparently less than that of ordinary amphotericin B, so as to effectively reduce the renal toxicity.

TABLE

The amphotericin B concentration in serum and organs of mouse in different time (ug/g)

| Injection time(h) | Serum | | Liver | | Kidney | | Spleen | |
|---|---|---|---|---|---|---|---|---|
| | Group A | Group B | Group A | Group B | Group A | Group B | Group A | Group B |
| 0.5 | 0.14 | 0.08 | 0.09 | 0.02 | 0.03 | 0.13 | 0.38 | 0.13 |
| 1.0 | 0.11 | 0.08 | 0.08 | 0.01 | 0.04 | 0.11 | 0.24 | 0.11 |
| 1.5 | 0.09 | 0.07 | 0.06 | 0.01 | 0.02 | 0.09 | 0.16 | 0.09 |
| 2.0 | 0.07 | 0.06 | 0.05 | 0.01 | 0.01 | 0.10 | 0.15 | 0.09 |
| 5.0 | 0.07 | 0.05 | 0.05 | 0.01 | 0.01 | 0.08 | 0.10 | 0.07 |

Example 23 Beneficial Effect of Drug Carrier (Active Targeting of Drug)

(1) Inoculate human hepatoma cell line BEL-7402 below back skin of BALB/C nude mouse. When tumor diameter is around 1 cm, take fresh tumor tissue like fish meat to slice into 1 mm*2 mm tumor block, and implant the block with ophthalmology tweezers inside tunnel below left outer lobe diolame of nude mouse, then seal the abdomen after hemostasis with cotton swab pressing slightly;

(2) Paunch to investigate in the 12$^{th}$ day after model making, select 20 model mice with tumor of basic consistent size, and divide them into group A and B, 10 mice for each group. Inject 0.2 ml adriamycin amycin drug carrier with targeting obtained in the example 15 through intraperitoneal injection every day for group A, and inject 0.2 ml adriamycin amycin obtained from the market as control through intraperitoneal injection every day;

(3) After 10 d, implement laparotomy for model mice to measure tumor size, and use tumor tissue for pathological section and point observation. The results show that the tumor inhibitory rate of sample group is higher than that of control group.

| | Weight (g) | | Tumor (mm³) | |
|---|---|---|---|---|
| | Before treatment | After treatment | Before treatment | After treatment |
| Adriamycin amycin-biomembrane | 20.53 | 21.46 | 43.62 | 30.12 |
| Adriamycin amycin | 20.03 | 20.1 | 42.93 | 50.17 |

Example 24 Beneficial Effect of Transgenosis (Effectiveness of Transfection Reagent)

(1) Inoculate U2OS cell on 6-hole plate to cultivate under the conditions of 37° C., 5% $CO_2$ in DMEM complete medium (including serum) for 24 hours;

(2) Add the transfection vector of packaged GFP obtained in the example 10 into serum-free DMEM medium with volume ratio of 1:9, then slightly blend evenly;

(3) Apply serum-free DMEF culture solution of vector including GFP gene on CHO cell evenly, and cultivate in cell incubator (37° C., 5% $CO_2$) for 6 hours, then add DMEM culture solution with 20% of fetal calf serum to continue to cultivate for 48 hours;

(4) The results in FIG. 3 show that green fluorescence can be seen under fluorescence microscope 48 after cell transfection, which indicates that the transfection is successful.

Example 25 Beneficial Effect of Transgenosis (Improving Transfection Efficiency)

Figure 4:
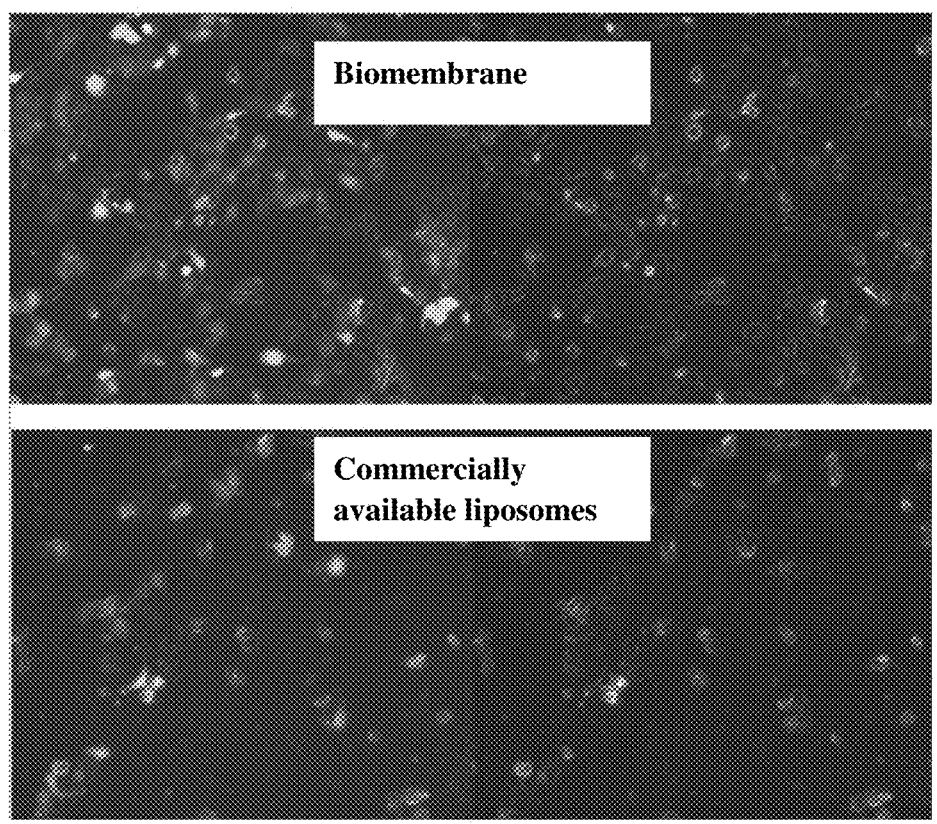
FIG. 4 shows the result of biomembrane as a transfection reagent for improving efficiency of transfection effectively.

(1) Purchase lipofection transfection agent from market to make it as control according to the proportion of example 24;

(2) The results in FIG. 4 show that biomembrane can be used as transfection agent to effectively improve transfection efficiency.

Example 26 Beneficial Effect of Transgenosis (Reducing Cytotoxicity)

(1) Digest the two groups of cells of example 25 with pancreatin 72 hour after transfection, and detect apoptosis of different transfection groups via flow cytometry after PI dyeing;

(2) The results show that biomembrane act as transfection reagent of biomembrane, which will cause that apoptosis rate is obviously less than . . . ; lipidosome acting as transfection reagent can effectively reduce cytotoxicity.

Example 27 Beneficial Effect of Cosmetics Additive (Preserving Moisture)

(1) Choose 10 persons randomly, then apply biomembrane obtained in example 4 which redissolve into 500 ul PBS on any side of hand at place of 10 cm×10 cm selected at back of left and right hand for each person, and apply the PBS of the same volume as control;

(2) 2 weeks after successively applying at the same place of the two hands, test with skin moisture tester the water content of skin of two sides;
(3) The results show that the average water content of skin for the back of hands which is applied by biomembrane is 48%, and that of hands which is applied by PBS is 43%, therefore biomembrane acting as cosmetics additive can effectively preserve moisture of skin.

Example 28 Beneficial Effect of Cosmetics Additive (Skin Whitening)

(1) Taking 0.5 mmol/L L-DOPA as substrate, add 20 uL cellular compartment (dissolved into DMSO solution) obtained in example 8 into 1.5 mL pear-shaped tube in the test system of 1 mL 0.05 mol/L phosphate buffer solution, than add 400 uL substrate solution which is placed in 30° C. thermostatic waterbath in advance for heat preservation, and supplement buffer solution so that the volume is up to 970 uL, then add 30 uL tyrosinase aqueous solution to shake evenly immediately, with PBS as control. And determine the increase straight line of light absorption value with time as wavelength is 475 nm within 1 min under the condition of 30° C. constant temperature, so that the enzyme activity is obtained from straight slope;
(2) The results show that the inhibition activity of cellular compartment to tyrosinase is 37%, while the inhibition of tyrosinase of control group is hardly obvious, biomembrane acting as cosmetics additive can effectively promote skin whitening.

Example 29 Beneficial Effect of Cosmetics Additive (Anti-Aging)

(1) Choose 10 persons randomly with age of 45-55, then apply biomembrane obtained in example 4 which redissolve into 500 ul PBS on any side of hand at place of 10 cm×10 cm selected at back of left and right hand for each person, and apply the PBS of the same volume as control;
(2) 4 weeks after successively apply at the same place for two hands, test with skin elasticity tester the anti-aging situation of skin;
(3) The results show that the skin elasticity of the back of hand which is applied with biomembrane is 30%, that of hand which is applied with PBS is 27%, therefore biomembrane acting as cosmetics additive can effectively anti aging.

Example 30 Beneficial Effect of Cosmetics Carrier (Improving Stability of Functional Component)

The same as example 16.

Example 31 Beneficial Effect of Cosmetics Carrier (Improving Solubility of Functional Component)

The same as example 16.

Example 32 Beneficial Effect of Cosmetics Carrier (Improving Long Residual Action of Functional Component)

Figure 5:
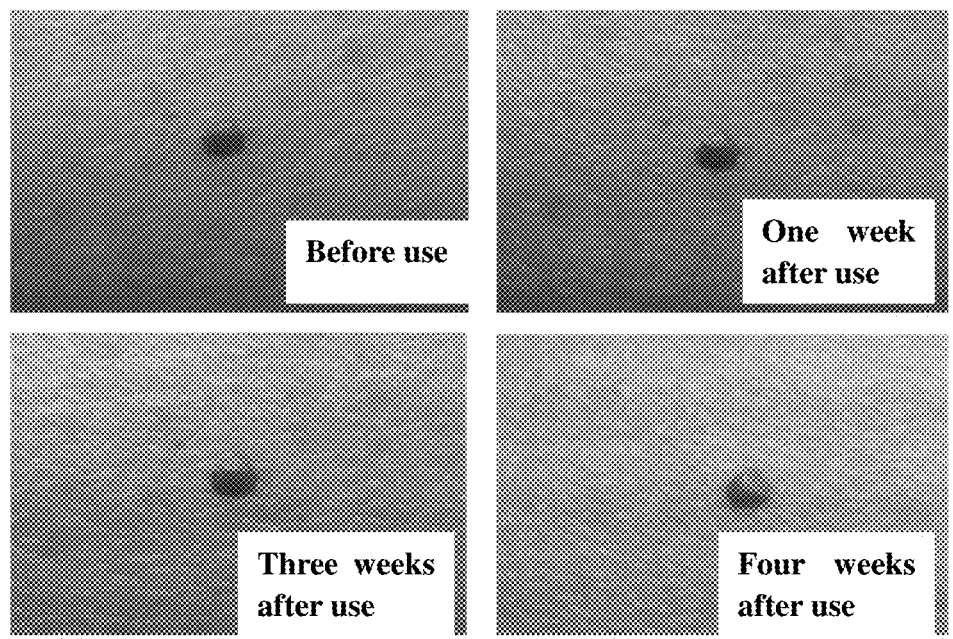
FIG. 5 shows the result of phenylethyl resorcinol packaged by biomembrane for a long-term whitening effect.

Reverse evaporating method is used to package drug in biomembrane, the specific steps are as follows:
(1) Dissolve the biomembrane obtained in example 6 mentioned above into chloroform with volume ratio of 4:1, then implement decompression rotary evaporation on rotary evaporator (37° C., 200 rpm) to remove chloroform;
(2) Dissolve Phenylethyl Resorcinol into ethyl alcohol, add ether to dissolve biomembrane in the step (1), and blend it with Phenylethyl Resorcinol with volume ratio of 1:10 to place in 50° C. waterbath for incubation for 20 min to get the cosmetics carrier packaged Phenylethyl Resorcinol;
(3) After demulsification of the cosmetics carrier packaged Phenylethyl Resorcinol obtained from the abovementioned steps, determine the content of Phenylethyl Resorcinol by means of High Performance Liquid Chromatography method, then dilute it with PBS to concentration of 0.5%;
(4) Select a piece of 10 cm×10 cm skin to apply 1 mL cosmetics carrier packaged Phenylethyl Resorcinol obtained from the abovementioned step (3), once in the morning and evening respectively per day;
(5) The results in FIG. 5 show that Phenylethyl Resorcinol of packaged biomembrane can long-term effectively whiten skin.

Example 33 Beneficial Effect of Cosmetics Carrier (Improving Absorption of Functional Component)

Figure 6:
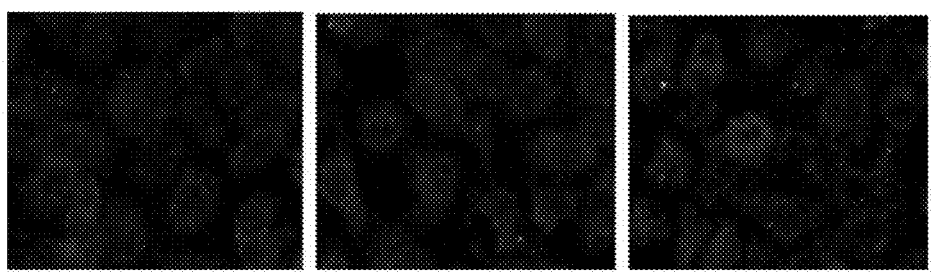
FIG. 6 shows the result of biomembrane for packaging curcumin as a carrier in significantly improving the cell absorption rate.
Figure 6:
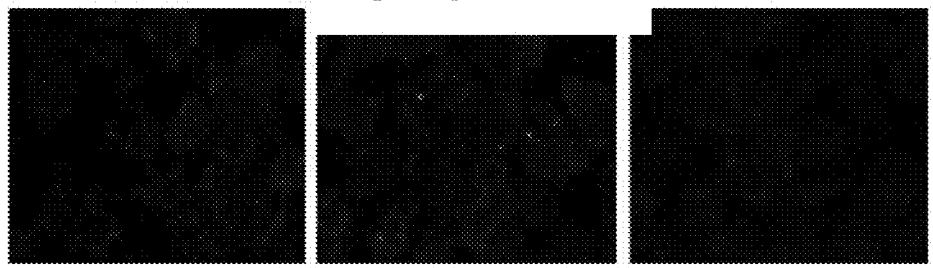

(1) Collect logarithmic phase B16 melanoma cell, adjust cell suspension concentration and add 500 μL cell suspension into each hole in 24-hole plate, place it horizontally to adjust the cell density to 50000/hole, stay it overnight for incubation and culture under the condition of 5% $CO_2$, 37° C.;
(2) Add the groups of samples of example 16 into cell medium respectively, with concentration of 500 nmol/L, then detect the centrocytes entering 5 hours later, and take photo for recording through fluorescence microscope;
(3) The results in FIG. 6 show that biomembrane acting as carrier to package curcumin can obviously improve cell absorption rate.

Example 34 Beneficial Effect of Cosmetics Carrier (Improving Effectiveness of Functional Component)

Figure 7A:
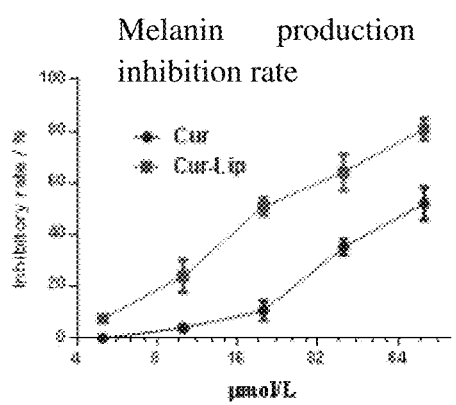
FIGS. 7A and B shows the result of biomembrane for packaging curcumin as a carrier in significantly inhibiting cell melanin.
Figure 7B:
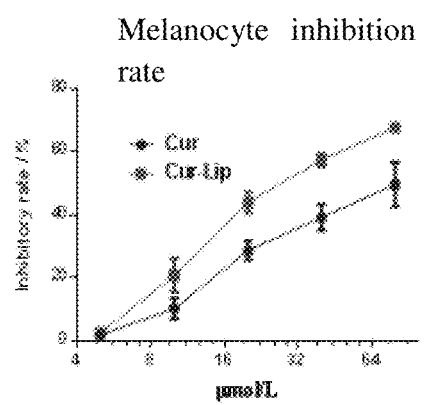

(1) Inoculate B16 melanophore in 6-hole plate, and cultivate it in DMEM complete medium (including serum) under the condition of 37° C., 5% $CO_2$ for 24 hours, then remove supernatant;
(2) Add the carrier of packaged curcumin obtained in the example 11 into serum-free DMEM medium, then slightly shake evenly, and take ordinary curcumin as control;
(3) Apply the serum-free DMEM culture solution with curcumin carrier evenly on B16 melanophore. 3 days after cultivating in cell incubator (37° C., 5% $CO_2$), remove supernatant, wash with PBS, add pancreas digestive cell in each hole for 5 min, then count for each group of cells respectively;
(4) Centrifuge the cell suspension under the condition of 20,000×g, 4° C. for 15 min, then remove supernatant, precipitate it, then add 1 mol/L NaOH solution, heat it to 80° C. for 30 min, and detect absorbancy of 475 nm with spectrophotometer;
(5) Inhibition ratio of melanin synthesis can be computed through formula: Inhibition ratio of melanin synthesis= [1−(absorbance value of drug hole/numbers of cell for drug hole)/(absorbance value of control hole/numbers of cell for control hole)]×100%. (FIGS. 7A and B)

Example 35 Beneficial Effect of Vaccine Carrier and Adjuvant (Safety)

In order to determine the substance which causes anaphylaxis exists in biomembrane as vaccine carrier or immunity adjuvant, and ensure the safety of biomembrane vaccine inoculation, the patent implement animal allergy test.
(1) Inoculate cellular compartments obtained from example 7 and 8 respectively with guinea pig, 2 for each group. Inoculate 1 mL to each guinea pig subcutaneously, with interval of one week, then implement subcutaneous vaccination for second time to
(2) The results show that after intravenous injection, all of guinea pigs do not appear to be dysphoria, shock, or death, which indicates that injection does not cause anaphylaxis for guinea pig.

Example 36 Application of Vaccine (Preventing from Virus Vaccine, Subcutaneous Form)

(1) Select a batch of health BALB/c mice with age of 6-8 weeks, 8 mice for each group;
(2) Include the carrier of packaged annulus virus obtained from example 12 into immunity group A, include annulus vaccine obtained from market into immunity group B as control, then inject 0.2 mL vaccine through intraperitoneal injection for the two groups of tested mice;
(3) Feed them under the same feeding and management condition. 21 days after immunity, inject 0.45 mL PCV2 virus ($10^{7.0}$TCID$_{50}$/mL) through ($10^{7.0}$TCID$_{50}$/mL) for counteracting toxic substances;
(4) 21 days after counteracting toxic substances, kill them to take spleens, blindly pass spleen suspension for 3 generations through PK15, and detect fluorescence with IFA. A lots of fluorescence quantity presents strong positive on virus separation, and bad immunity effect.

| Grouping | Quantity of fluorescence immunity fluorescence test samples (repeated two-hole statistic results) | | | | | | | |
|---|---|---|---|---|---|---|---|---|
| Group A | (4, 3) | (2, 1) | (2, 0) | (1, 1) | (0, 1) | (1, 0) | (0, 0) | (0, 0) |
| Group B | (2, 6) | (2, 5) | (2, 2) | (2, 2) | (3, 0) | (2, 1) | (1, 2) | (2, 0) |

Example 37 Application of Vaccine (Gene Vaccine, Intramuscular Injection)

(1) Select ten beagles with an average weight of 3 kg (2.5-3.5 kg), and without limitations on gender. Divide them randomly into group A and group B, 3 beagles for each group.
(2) Inject group A with biomembrane intramuscular injection which packaged hundestaupe virus DNA plasmid (refer to methods in example 12), 500 ul biomembrane vaccine with plasmid DNA concentration of 1 ug/ul for each beagle. Inject group B with hundestaupe virus DNA plasmid with same DNA concentration as control, injecting one vaccine for every two weeks;
(3) Two weeks after the third vaccine, using double-resistance treated 1:10 diluent of cerebral homogenate of canine distemper onset beagle to do challenge assay upon all experimental beagles with 2 mL for each beagle, of which 1 mL is nasal inhalation, and 1 mL is intramuscular injection;
(4) Measure the rectal temperature everyday after challenge assay, making detailed record on the morbidity and death status of the experimental beagles, observing the development of clinical symptoms.
(5) Two experimental beagles died after challenge assay, the rest one appeals slight neurological sign with the highest animal heat up to 41° C., then slowly lapse to normal. Biomembrane injection group also appeal animal heat going up at different degree with the highest up to 39.4° C., but no neurological sign and death.
(6) The result reveals that biomembrane, as the carrier of gene vaccine and immunologic adjuvant, has strong immune effect.

Example 38 Application of Vaccine (Tumor Vaccine, Oral Delivery)

(1) Ten healthy mice with weight of 18-22 g, no limitations on gender, are randomly divided into Group A and Group B with 5 mice for each;
(2) Mice should be on fasting and water-fast for more than 12 hours before vaccine and inoculation, and 30 min before inoculation orally feed it 150 L 0.01 mol/L NaHCO$_3$ solution to neutralize gastric acid. Orally feed Group A with biomembrane carrier vaccine that is packaged *Helicobacter pylori* recombinant protein (refer to example 12), and feed each mouse 100 uL biomembrane vaccine with 10 uL of *Helicobacter pylori* recombinant protein. Feed Group B 100 uL PBS, which has *Helicobacter pylori* recombinant protein 10 uL as control.
(3) Test group and control group immunize once respectively at $0^{th}$, $7^{th}$, $14^{th}$, $21^{st}$ day. Regain food and water 1 hour after vaccine. Each group use *Helicobacter pylori* with $10^8$ CFU/time to attack two weeks after the last vaccine ($35^{th}$ day), once every other day, totally 3 times, and kill the mice 4 weeks after the last attack.
(4) Laparotomize the mice immediately after killed to take stomach and spleen, scissoring along greater curvature side and washing gastric contents with stroke-physiological saline solution, taking gastric tissue along vertical axis, smear and place on 96-well plates for rapid urease test.
(5) The urease test shows: compared with the control group, biomembrane vaccine group can better prevent laboratory mice from infection of *Helicobacter pylori*, which is the important pathogenic factor for diseases such as gastric cancer, gastric mucosal tissue lymphoma and etc. Therefore using biomembrane as the vaccine carrier and adjuvant of *Helicobacter pylori* recombinant protein can effectively prevent diseases such as gastric cancer, etc.

Example 39 Beneficial Effect of Vaccine Carrier and Adjuvant (Strongly Effective Humoral Immunity)

The same with example 36

Example 40 Beneficial Effect of Vaccine Carrier and Adjuvant (Strongly Effective Cellular Immunity)

(1) Comparing expression of splenic lymphocyte INF-γ and IL-4 mRNA of mice spleen that is acquired from example 38;

(2) The result displays that mice spleen lymphocyte appears hyperplasia majored with Th1 cell (INF-γ), and INF-γ level has significant difference when contrast with the control group, by using vaccine carrier and adjuvant taking biomembrane as the *Helicobacter pylori* recombinant protein.

Example 41 Application of Artificial Organ (1) Select ten two-months-years-old beagles with an average weight of 2.5 kg (2-3 kg), without limitation of female or male, and divide randomly into two groups A and B, with 5 for each group.
(2) Cut open knee joint capsule from outside of the right knee of beagle, without cutting off collateral ligaments, and make a triangle coloboma (bottom edge is at periphery and tip toward half of the width of somatic part of meniscus), then make a column coloboma at ischemic region.
(3) Group A implant the artificial meniscus acquired from Example 13 into coloboma. Group B implant artificial meniscus which is supported by collagen, and is acquired from the market into coloboma as contrast. Both of the two groups suture and fix with 5-0 absorbable suture, and then suture the incision, cage culture after operation.
(4) Kill the animal in the $12^{th}$ week after operation, and take the knee-joint sample for observation: well union at coloboma can be seen for Group A, and white cambium can be seen growing in coloboma area, which the texture and color are similar with surrounded normal meniscus tissues with no distinct demarcation. Group B can see texture and color around the implant are similar with normal meniscus, and white fiber scar tissues can be seen in coloboma area, and correspondent thighbone and tibia articular surface appear to be a bit rough.

The invention shown and described herein may be implemented in the absence of any elements, limitations specifically disclosed herein. The terms and expressions used herein are used as illustrative and not restrictive, and not intended to exclude any equivalents of the features and parts thereof described herein in the use of such terms and expressions; moreover, it is to be understood that various modifications are feasible within the scope of the present invention. It is therefore to be understood that, although the invention has been particularly disclosed by various embodiments and alternative features, modifications and variations of the concepts described herein may be employed by those skilled in the art, and these modifications and variations will fall within the scope of the invention as defined by the appended claims.

The contents of the articles, patents, patent applications, and all other documents and electronic information available or documented herein are incorporated herein by reference in their entirety and are hereby incorporated by reference as if each individual publication is specifically and individually indicated for reference. The applicant reserves the right to incorporate any and all materials and information from any such article, patent, patent application or other document into this application.

The following numbered paragraphs describe particular aspects and embodiments of the present invention:
1. A method of preparing a biomembrane in vitro, comprising the steps of: 1), acquiring biological cells from natural tissues or natural biological species; 2), culturing the cells obtained in step 1) massively in an appropriate environment; 3), acquiring the lysates of the cells in step 2), then carrying out separation and purification in vitro with different methods to obtain various biomembranes or mixtures; the methods for acquiring biomembranes in vitro herein include differential centrifugation, density gradient centrifugation and dual-phase extraction, individually or a combination of two methods or a combination of three methods thereof, to extract the desired biomembranes.
2. The method according to paragraph 1, wherein the differential centrifugation extraction method comprises the following steps: centrifuge the cell lysate at the first high-speed to obtain a supernate and then certrifuge the supernate at a second speed less than the first high-speed to get the precipitate as the desired biomembranes.
3. The method according to paragraph 2, wherein the first high-speed is 1.5, 1, 2 or 3 times of the second speed.
4. The method according to paragraph 2, wherein the centrifugation is carried out at 15,000-30,000×g, 1-6° C. for 10-30 min to discard precipitate and collect supernate; then the supernate is ultra-centrifuged at 100,000-200,000×g, 1-6° C. for 30-90 min, to discard the supernatant and collect the precipitate, to get the extracted biomembrane.
5. The method according to paragraph 1, wherein the density gradient centrifugation method comprises the following steps: resuspend the resulting cell lysate precipitate, and add the resuspension solution to different concentrations of sucrose solution, to ultra-centrifuge at 150,000-300,000×g, 1-6° C. for 60-90 min and collect the supernate; then ultra-centrifuge the collected liquid at 100,000-200,000×g, 1-6° C. for 30-90 min, discard the supernatant and collect the precipitate, to get the extracted biomembrane.
6. The method according to paragraph 1, wherein resuspend the resulting cell lysate precipitate, and add a first concentration of sucrose solution, a second concentration of sucrose solution and a third concentration of sucrose solution successively, and the first concentration is less than the second concentration and the third concentration is less than the first concentration.
7. The method according to paragraph 5, wherein the sucrose solution has a mass percent concentration in the range of 10% to 70%; preferably, the different mass percent concentrations of sucrose solution in step 3 are 10%, 20%, 30%, 40%, 45%, 50%, 55%, 60%, 65%, 70%; or the molar concentration of a first concentration of sucrose solution is 0.1-0.5 mol/L, the molar concentration of a second concentration of sucrose solution is 1-3 mol/L; and the molar concentration of a third concentration of sucrose solution is 0.01-0.3 mol/L.
8. The method according to paragraph 1, wherein the density gradient centrifugation extraction process comprises the steps: re-suspend the obtained cell lysate precipitation, after multiple times of centrifugation at first low-speed, collect the precipitate 1 to prepare suspension 1, then centrifuge the suspension 1 at a second high-speed for many times to get precipitate 2, and then suspend the precipitate 2 using a nonionic surfactant solution to get the suspension 2, at the same time, dilute suspension 2 with sucrose solution, transfer the diluted suspension 2 to the bottom of a centrifuge tube, and add high concentration and low concentration of sucrose solutions successively, centrifuge at a high speed (eg 28000×g-45,000×g) for 10-24 h at 4° C., and collect the desired biomembrane at the interface of high and low concentrations.
9. The method according to paragraph 8, wherein the high concentration of sucrose is 20-35%, and the low concentration of sucrose is 2-10% (in mass percent).

10. The method according to paragraph 1, wherein the dual-phase extraction method comprises the following features:

freshly prepare the dual-phase system; then re-suspend the cell lysate precipitation and add to the dual-phase mixture, gently mix them upside down for 30-40 times evenly; centrifuge at 2,000-4.000× for 5-10 min at 4° C., take the top phase and bottom phase to the two-phase system, to separate three times and combine the top phases, after diluted by 5-fold, centrifuge at 60,000-100.000×g for 30-90 min at 4° C., collect the precipitate, to get the biomembrane to be extracted.

11. The method according to paragraph 10, wherein the dual-phase comprises an aqueous dual-phase or an organic dual-phase, an aqueous phase solution and an organic phase solution, and the solvent is selected from any one of water, acetonitrile, acetone, tetrahydrofuran, methanol, ethanol, propanol, or a combination thereof.

12. The method according to paragraph 10, wherein the dual-phase is a dual-phase mixture of dextran/polyethylene glycol.

13. A method of preparing a biomembrane having self-assembly, wherein the method comprises the following steps: cover the materials of the acquired biomembrane, closed structure with the biomembrane characteristics and cellular compartment on the container wall in a form of dry membrane, then slowly inject water or buffer solution, slightly or violently vibrate, to get the required biomembrane, closed structure with biomembrane characteristics and cellular compartment by self-assembly.

14. The method according to paragraph 13, wherein the materials of the required biomembrane, closed structure with the biomembrane characteristics and cellular compartment are firstly dissolved in an organic solvent, added to the container, evaporated under reduced pressure to make the biomembrane spread on the container surface, after evaporated to constant weight, PBS buffer solution is added and slowly shaken 0.5~3 h, ultra-centrifuged at 100,000~200,000×g for 30~90 min at 1~6° C., to discard the supernatant and collect the precipitates, to get the required biomembrane, closed structure with biomembrane characteristics and cellular compartment.

15. The method according to paragraph 14, wherein the organic solvent is chloroform or ether.

16. The method according to paragraph 14, wherein the biomembrane is the one acquired through one of paragraphs 1 to 12.

17. The method according to paragraph 1, wherein the natural biomembrane is from plants, animals or microbes; the natural tissue is a fresh blood or *Thermus Thermophillus*.

18. The method according to paragraph 1, wherein the biomembranes include spherical, vesicular, rod-shaped, spiral single-layer or multi-layer, multi-chamber morphological structures according to shapes; and include one or more from plasma membrane, nuclear membrane, mitochondrial membrane, endoplasmic reticulum, lysosomal membrane, Golgi membrane, chloroplast membrane and vacuole and peroxisome membrane, or the biomembranes include cellular compartments, and the cellular compartments are organelles; more preferably, the cellular compartment is one or more from mitochondria, chloroplasts, peroxisomes, lysosomes, endoplasmic reticulum, nucleus, Golgi and vesicles and microtubules.

19. The method according to paragraph 18, wherein the method further comprises preparing the cellular compartment, and the method comprising: preparing a two-phase system.

20. The method according to paragraph 19, wherein the two-phase system is an aqueous dual-phase system, comprising the following steps: (1) mix the mixture (containing 90 g 20% (W/W) Dextran T-500, 45 g 40% (W/W) PEG 3350, 33.9 g sucrose, 7.5 g 0.2 mmol/L PBS, 0.45 g 2 mmol/L KCl per 300 g) uniformly, to make equal concentration of aqueous dual-phase mixture of dextran/polyethylene glycol (Dextran T-500/PEG 3350), mix well in a separatory funnel, standing for layering at 4° C. overnight, carefully separate the upper and lower layers, to prepare fresh top phase and bottom phase, then store in 4° C. respectively for the subsequent purification; (2) re-suspend the biomembrane precipitate obtained in paragraph 1 using resuspension buffer (5 mmol/L PBS, 0.33 mol/L sucrose, 3 mmol/L KCl, 1 mmol/L DTT, 1 mmol/L PMSF, 0.1 mmol/L EDTA); (3). Add the above re-suspension to the aqueous dual-phase mixture of Dextran T-500/PEG 3350 prepared in step (1) according to a mass ratio of 1:3, gently reverse 30-40 times to mix well; (4) centrifuge the mixed solution at 1,500 rpm for 10 min at 4° C., continue to take the top phase solution and bottom phase solution to the two-phase system, after separated 3 times, combine the top phase separation solution, dilute 5 times, centrifuge at 100,000×g for 60 min at 4° C. and collect the precipitate, to get the required cellular compartment.

21. The method according to paragraph 18, wherein when the natural material is spinach, the method for acquiring cellular compartments comprising: (1) select 10 g of spinach leaves with healthy growth, and preferably growing in several successive sunny days, wash clean to remove midrib, add 6-fold homogenate buffer (by volume) (50 mmol/L potassium phosphate buffer, 0.3 mmol/L sorbitol, 2 mmol/L EDTA, 1 mmol/L $MgCl_2$, 1 mmol/L MnCl2, 1% BSA, 1 mmol/L DTT) according to the mass/volume ratio, and grind under ice bath; (2) prepare the Percoll separating solution (50 mmol/L HEPES-KOH, 0.3 mmol/L sorbitol, 2 mmol/L EDTA, 1 mmol/L $MgCl_2$, 1 mmol/L $MnCl_2$, 1% BSA, 3% PEG 6000, 1% Ficoll), pre-centrifuge at 30,000×g for 20 min at 4° C.; (3) filter the grinding fluid through a four-layer gauze, centrifuge at 30,000×g for 15 min at 4° C., collect the precipitate, and suspend the precipitate with 2 ml homogenate buffer, and place to the Percoll separating solution centrifuged in step (2), centrifuge at 15,000×g for 20 min at 4° C., such the lower layer, to get the required cellular compartment.

22. The preparation method according to paragraph 1, wherein when the cells are from fresh blood, the method comprising the steps: (1) centrifuge 30 mL of fresh blood at 100×g for 10 min at 4° C., suck the plasma and floccules on the erythrocyte surface layer with a sucker; (2) add 5-fold of pH 8.0 PBS buffer (by volume), centrifuge at 2,000×g for 15 min at 4° C., to discard the supernate, repeat 3 times; (3) add 40-fold pH 8.0 PBS buffer (by volume) to the precipitate, stand 2 h for hemolysis at 4° C.; (4) centrifuge at 22,000×g for 20 min at 4° C., repeat 4 times; (5) resuspend the precipitate with a pre-cooled Triton X-100 buffer (containing 0.25 mmol/Lsucrose, 150 mmol/LNaCl, 1 mmol/LEDTA, 20 mmol/L Tris-HCl and 1% Triton X-100), then dilute with equal volume of 80% (W/V) sucrose solution; (6) Transfer 4 mL of membrane suspension to the bottom of the centrifuge tube, then add 4 mL of 30% and 3 mL of 5% sucrose solution, centrifuge at 38,000×g for 18 h at 4° C., collect at the interface of 5% and 30% sucrose, to get the required biomembrane.

23. The preparation method according to paragraph 1, wherein when the cells are derived from *Thermus Thermophillus*, the method comprising the steps: (1) *Thermus*

Thermophillus is separated and purified from U.S. Yellowstone National Park Spa Pool; (2) inoculate Thermus Thermophillus to a medium according to the ratio of 1:100 (10 L of medium contains 26 g (NH4)2SO4, 2.47 g MgSO4.7H2O, 2.8 g KH2PO4, 0.74 g CaCl2.2H2O, 0.19 g FeCl3.6H2O, 0.018 g MnCl2.4H2O, 0.044 g Na2B4O7.10H2O, 0.002 g ZnSO4.7H$_2$O), place to an incubator and culture 24 h at 150 rpm, 60° C.; (3) centrifuge to collect thalli for 30 min at 4,000 rpm and 4° C.; (4) re-suspend thalli with a homogenate buffer (20 mmol/L Tris-Cl pH8.0, 100 mmol/L NaCl, 2 mmol/L MgCl2, 1 mmol/L DTT), centrifuge to discard the supernatant for 10 min at 6,000 rpm and 4° C.; (5) add homogenate buffer to re-suspend the precipitate (add 10 ml of buffer in about 1 g), then add PMSF with a final concentration of 1 mmol/L, break under ice bath and ultrasound condition (amplitude of 55%, ultrasound 5 s, stop 8 s); (6) centrifuge the broken thalli at 25,000×g for 30 min at 4° C., to discard the precipitate and collect the supernatant; (7) ultra-centrifuge the supernatant at 145,000×g for 1 h at 4° C., collect the precipitate to get the required biomembrane.

24. The method according to paragraph 1, wherein the method further comprises the steps of to carrying out the package of the active substance with the prepared biomembrane, the package method includes one or more from intracellular membrane package, intracellular membrane package, surface adsorption, surface cross-linking, inter-membrane embedding or intracellular membrane package plus targeting method.

25. The preparation method according to paragraph 24, wherein an active ingredient comprises a vaccine or active ingredient of immunoregulatory agents, a cosmetics or an active ingredient, a pharmaceutically active ingredient, a genetic material and cells or tissues.

The invention claimed is:

1. A method of preparing a biomembrane in vitro, comprising the following steps in sequence of:
   (1) inoculating *Thermus Thermophillus* in a medium of 10 L, the medium of 10 L comprises 26 g (NH4)$_2$SO$_4$, 2.47 g MgSO$_4$.7H$_2$O, 2.8 g KH$_2$PO$_4$, 0.74 g CaCl$_2$.2H$_2$O, 0.19 g FeCl$_3$.6H$_2$O, 0.018 g MnCl$_2$.4H$_2$O, 0.044 g Na$_2$B$_4$O$_7$.10H$_2$O, 0.002 g ZnSO$_4$.7H$_2$O, placing the medium comprising *Thermus Thermophillus* to an incubator and culturing 24 h at 150 rpm, 60° C.;
   (2) centrifuging the medium from step (1) for 30 min at 4,000 rpm and 4° C. to collect thalli;
   (3) resuspending the thalli with a homogenation buffer as to form a first mixture, wherein the buffer comprises 20 mmol/L Tris-Cl pH8.0, 100 mmol/L NaCl, 2 mmol/L MgCl$_2$, 1 mmol/L dithiothreitol, centrifuging the first mixture for 10 min at 6,000 rpm and 4° C. as to form to a supernatant and a precipitate, discarding the supernatant;
   (4) adding the homogenation buffer to resuspend the precipitate with the ratio of the buffer to the precipitate of 10 ml:1 g, adding phenylmethylsulfonyl fluoride to reach a concentration of 1 mmol/L to form a second mixture, placing the second mixture under ice bath under ultrasound condition with amplitude of 55%, ultrasound 5 s, stop 8 s as to form a broken thalli;
   (5) centrifuging the broken thalli at 25,000×g for 30 min at 4° C., discarding the precipitate, and collecting the supernatant; and
   (6) ultra-centrifuging the supernatant at 145,000×g for 1 h at 4° C., collecting the precipitate to get the biomembrane.

2. The method according to claim 1, wherein the biomembranes comprises spherical, vesicular, rod-shaped, spiral single-layer or multi-layer, multi-chamber morphological structures; the biomembrane further comprises one or more from plasma membrane, nuclear membrane, mitochondrial membrane, endoplasmic reticulum, lysosomal membrane, Golgi membrane, chloroplast membrane and vacuole and peroxisome membrane.

3. The method according to claim 1, wherein the method further comprises a step of packing an active substance with the biomembrane, the step of packing includes one or more from intracellular membrane package, intracellular membrane package, surface adsorption, surface cross-linking, inter-membrane embedding or intracellular membrane package plus targeting method.

4. The method according to claim 3, wherein the active substance is one member selected from the group consisting of a vaccine, an active ingredient of immunoregulatory agents, a cosmetic, a pharmaceutically active ingredient, a genetic material, cells and tissues.

* * * * *